US012643865B2

(12) United States Patent
Herrmann et al.

(10) Patent No.: US 12,643,865 B2
(45) Date of Patent: Jun. 2, 2026

(54) COMPOUNDS FOR PROVIDING A LONG-LASTING ODOR

(71) Applicant: Firmenich SA, Satigny (CH)

(72) Inventors: Andreas Herrmann, Satigny (CH); Serge Lamboley, Satigny (CH)

(73) Assignee: FIRMENICH SA, Satigny (CH)

( * ) Notice: Subject to any disclaimer, the term of this patent is extended or adjusted under 35 U.S.C. 154(b) by 685 days.

(21) Appl. No.: 17/801,143

(22) PCT Filed: Apr. 12, 2021

(86) PCT No.: PCT/EP2021/059457
§ 371 (c)(1),
(2) Date: Aug. 19, 2022

(87) PCT Pub. No.: WO2021/209396
PCT Pub. Date: Oct. 21, 2021

(65) Prior Publication Data

US 2023/0091481 A1 Mar. 23, 2023

(30) Foreign Application Priority Data

Apr. 14, 2020 (EP) .................................... 20169432

(51) Int. Cl.
*C07D 235/02* (2006.01)
*C07D 263/52* (2006.01)
*C07D 487/04* (2006.01)

(52) U.S. Cl.
CPC ......... *C07D 235/02* (2013.01); *C07D 263/52* (2013.01); *C07D 487/04* (2013.01)

(58) Field of Classification Search
CPC ... C07D 235/02; C07D 263/52; C07D 487/04
See application file for complete search history.

(56) References Cited

U.S. PATENT DOCUMENTS

2019/0175777 A1 6/2019 Iwai et al.

FOREIGN PATENT DOCUMENTS

| | | | |
|---|---|---|---|
| EP | 3467078 | A1 | 4/2019 |
| JP | 2002528441 | A | 9/2002 |
| JP | 2017210589 | A | 11/2017 |
| WO | 2000024721 | A2 | 5/2000 |
| WO | 2020/058058 | A1 | 3/2020 |
| WO | 2020/078892 | A1 | 4/2020 |

OTHER PUBLICATIONS

Buchs, et al. European Journal of Organic Chemistry (2011), (4), 681-695; retrieved from STN; Accession No. 2011:95434.*

Buchs, B, et al. "Reversible Aminal Formation: Controlling the Evaporation of Bioactive Volatiles by Dynamic Combinatorial/Covalent Chemistry" Eur. J. Org. Chem. v2011:4 pp. 681-695, (2011).

Belsito, D., et al., "A toxicologic and dermatologic assessment of cyclopentanones and cyclopentenones when used as fragrance ingredients", Food and Chemical Toxicology, 50:S517-S556 (2012).

* cited by examiner

*Primary Examiner* — Shawquia Jackson

(57) ABSTRACT

The present invention relates to the field of perfumery. More particularly, it relates to compounds of formula (I) that are able to provide a long-lasting or substantive odor to the environment. Moreover, the present invention relates to a method of imparting a long-lasting odor to environment or to surfaces, such as hard surfaces, fabric, skin or hair. Furthermore, the present invention relates to the use of said compounds in perfumery, as well as the perfuming compositions or perfumed articles comprising the invention's compounds.

20 Claims, No Drawings

COMPOUNDS FOR PROVIDING A LONG-LASTING ODOR

This present application is a U.S. national phase entry under 35 U.S.C. § 371 of PCT Application No. PCT/EP2021/059457, filed Apr. 12, 2021, which claims priority to European Patent Application No. 20169432.0, filed Apr. 14, 2020. The entire contents of these applications are explicitly incorporated herein by this reference.

TECHNICAL FIELD

The present invention relates to the field of perfumery. More particularly, it relates to compounds of formula (I) that are able to provide a long-lasting or substantive odor to the environment. Moreover, the present invention relates to a method of imparting a long-lasting odor to the environment or to surfaces, such as hard surfaces, fabric, skin or hair. Furthermore, the present invention relates to the use of said compounds in perfumery, as well as the perfuming compositions or perfumed articles comprising the invention's compounds.

PRIOR ART

Consumers often correlate the efficiency of perfumed articles with the long-lastingness or substantivity of perfume perception. Perfumes are composed of a multitude of different volatile compounds, which are applied to a surface from which they evaporate to be smelled. The perfume is applied to the environment or to surfaces, such as hard surfaces, fabric, skin or hair, via a perfume composition or a perfumed consumer article, as for example fine fragrances or shower gels. Due to the high volatility of the fragrances, which constitute perfumes, the odor emitted from the perfumed surface can only be perceived over a limited period of time. In particular, the so-called top-notes of a perfume evaporate quite rapidly. They are the most volatile compounds of the composition and represent the freshness of a perfume. Top-notes typically comprise, among others, citrus, flowery, green and fruity notes, and especially the floral and fruity notes are well-appreciated by the consumers. Several classes of floral and fruity notes are used in perfumes. Typical examples of fruity notes are those resembling of peach, apricot, and exotic fruits.

Consumers seek for fragrances that are stable in the targeted application and at the same time long-lasting or substantive to be smelled for several hours or even days after application. In particular long-lasting fruity and floral notes are desirable.

Therefore, it is the goal of the present invention to provide a system that is able to deliver a long-lasting or substantive odor, in particular a fruity and/or floral odor, to the environment. Furthermore, another objective of the present invention is to find a method of imparting a long-lasting odor of cyclopentanone-derived perfumery ingredients known for their fruity and/or floral organoleptic properties, to surfaces, such as hard surfaces, fabric, skin or hair, via the application of perfuming compositions or perfumed articles.

DESCRIPTION OF THE INVENTION

It has now been found that some specific compounds, namely multicyclic compounds derived from cyclopentanone-based perfumery ingredients, can advantageously be employed to bring a long-lasting or substantive perfume effect, in particular a fruity and/or floral note, from a given surface into the environment, and thus to be useful as ingredients for perfuming compositions or perfumed articles.

Therefore, a first object of the present invention is a compound of formula (I)

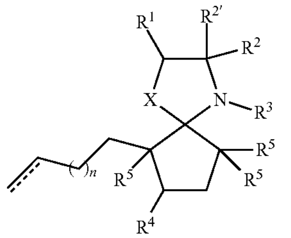

in the form of any one of its stereoisomers or a mixture thereof, and wherein n is 1, 2, 3 or 4;

the dotted line represents a single or a double bond,

X is an oxygen atom or a N—R group wherein R is a hydrogen atom, a $C_1$ to $C_4$ alkyl group, a phenyl group or a benzyl group, $R^1$ is a hydrogen atom or a $C_1$ to $C_{10}$ hydrocarbon group, optionally comprising from 1 to 5 oxygen atoms and/or one sulphur atom and/or one, two or three nitrogen atoms;

$R^2$ and $R^{2'}$ are, independently from each other, a hydrogen atom, a $C_1$ to $C_4$ alkyl group or a $CHR^1XH$ group, or $R^2$ and $R^{2'}$ when taken together form a carbonyl group;

$R^3$ is hydrogen atom, a $C_1$ to $C_4$ alkyl group, a phenyl group or a benzyl group;

$R^4$ is a hydrogen atom, a COOR' group or a $C_{1-3}$ alkyl group optionally substituted by a COOR' group wherein R' is a $C_{1-3}$ alkyl group;

$R^5$ are, independently from each other, a hydrogen atom or a methyl group; or

R and $R^1$, when taken together form a $C_{4-6}$ azocycloalkyl group; or $R^1$ and $R^2$; when taken together form a $C_{5-6}$ cycloalkyl group; or, $R^2$ and $R^3$, when taken together form a group of formula (II)

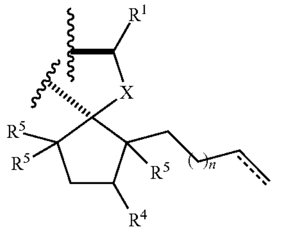

wherein the bold line is connected to the carbon atom of $R^2$ and the hatched line to the nitrogen atom of $R^3$.

For the sake of clarity, by the expression "any one of its stereoisomers or a mixture thereof", or the similar, it is meant the normal meaning understood by a person skilled in the art, i.e. that the compound of formula (I) can be a pure enantiomer (if optically active) or a diastereoisomer. In other words, the compound of formula (I) may possess several stereocenters and each of said stereocenter can have two different stereochemistries (e.g. R or S). The compound of formula (I) may even be in the form of a pure enantiomer or in the form of a mixture of enantiomers or diastereoisomers. The compound of formula (I) can be in a racemic form or scalemic form. Therefore, the compound of formula (I) can be one stereoisomer or in the form of a composition of matter comprising, or consisting of, various stereoisomers.

For the sake of clarity, by the expression "dotted line represents a single or a double bond", or the similar, it is meant the normal meaning understood by a person skilled in the art, i.e. that the whole bonding (solid and dotted line) between the carbon atoms connected by said dotted line is a carbon-carbon single or double bond.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that with the terms " . . . a hydrocarbon group, optionally comprising . . . " and " . . . a hydrocarbon group, optionally substituted with . . . " it is meant that said hydrocarbon group optionally comprises alcohol, ketone, aldehyde, ether, thioether, ester, carboxylic acid, amine, amide, carbamate, nitrile or thiol groups. These groups can either substitute a hydrogen atom of the hydrocarbon group and thus be laterally attached to said hydrocarbon, or substitute a carbon atom (if chemically possible) of the hydrocarbon group and thus be inserted into the hydrocarbon chain. For example, a $—CH_2—CH_2—CHOH—CH_2—$ group represents a $C_4$ hydrocarbon group comprising an alcohol group (substitution of a hydrogen atom), a $—CH_2—CH_2—COO—CH_2—CH_2—OCO—CH_2—CH_2—$ group represents a $C_6$ hydrocarbon group comprising two ester groups (substitution of carbon atoms/insertion into the hydrocarbon chain) and, similarly, a $—CH_2—CH_2—O—CH_2—CH_2—O—CH_2—CH_2—$ group represents a $C_6$ hydrocarbon group comprising two ether groups.

The term "alkyl" is understood as comprising branched and linear alkyl groups. The term "cycloalkyl" is understood as comprising monocyclic or multicyclic alkyl groups; i.e. compounds of formula (I) comprise a fused bicyclic group. The term "azocycloalkyl" is understood as comprising a ring made of carbon atoms and one nitrogen atom.

For the sake of clarity, by the expression "wherein the bold line is connected to the carbon atom of $R^2$ and the hatched line to the nitrogen atom of $R^3$" or the similar, it is meant the normal meaning understood by a person skilled in the art, i.e. the compound of formula (I) is of formula (III)

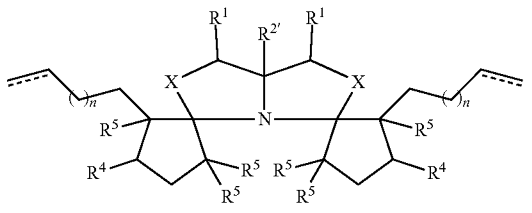

in the form of any one of its stereoisomers or as a mixture thereof, wherein the dotted line, n, X, $R^1$, $R^{2'}$, $R^4$ and $R^5$ have the same meaning as defined above.

According to any embodiments of the invention, the invention's compound is a compound of formula (I) as defined above, provided that 1,3-dibenzyl-2'-pentyloctahydrospiro[benzo[d]imidazole-2,1'-cyclopentane] is excluded.

According to any embodiments of the invention, each $R^5$ may be a methyl group or each $R^5$ may be a hydrogen atom. Particularly, each $R^5$ may be a hydrogen atom.

According to any embodiments of the invention, $R^3$ may be a hydrogen atom or a $C_1$ to $C_4$ alkyl group. Particularly, $R^3$ may be a hydrogen atom, a methyl or an ethyl group.

According to any embodiments of the invention, the invention's compound is a compound of formula (I')

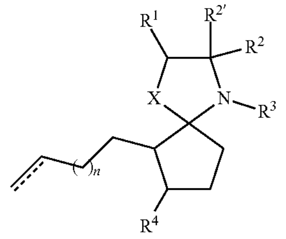

in the form of any one of its stereoisomers or a mixture thereof, and wherein n is 1, 2, 3 or 4;

the dotted line represents a single or a double bond

X is an oxygen atom or a N—R group wherein R is a hydrogen atom, a $C_1$ to $C_4$ alkyl group, a phenyl group or a benzyl group, $R^1$ is a hydrogen atom or a $C_1$ to $C_{10}$ hydrocarbon group, optionally comprising from 1 to 5 oxygen atoms and/or one sulphur atom and/or one, two or three nitrogen atoms;

$R^2$ and $R^{2'}$ are, independently from each other, a hydrogen atom, a $C_1$ to $C_4$ alkyl group or a $CHR^1XH$ group, or $R^2$ and $R^{2'}$ when taken together form a carbonyl group;

$R^3$ is hydrogen atom or a methyl group;

$R^4$ is a hydrogen atom, a COOR' group or a $C_{1-3}$ alkyl group optionally substituted by a COOR' group wherein R' is a $C_{1-3}$ alkyl group; or R and $R^1$, when taken together form a $C_{4-6}$ azocycloalkyl group.

According to any embodiments of the invention, $R^4$ may be a hydrogen atom, a methyl group, a $COOCH_3$ group or a $CH_2COOCH_3$ group. Particularly, $R^4$ may be a hydrogen atom.

According to any embodiments of the invention, n may be 2, 3 or 4, particularly, 2 or 3, even more particularly 3.

According to any embodiments of the invention, $R^3$ may be a hydrogen atom.

According to any embodiments of the invention, the invention's compound is of formula (IV)

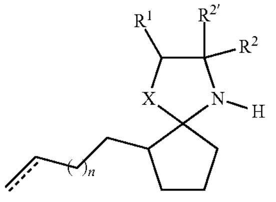

in the form of any one of its stereoisomers or as a mixture thereof, wherein the dotted line, n, $R^1$, $R^2$ and $R^{2'}$ have the same meaning as defined above.

According to any embodiments of the invention, X may be a N—R group wherein R is a hydrogen atom, a methyl or an ethyl group, particularly R may be a hydrogen atom.

According to any embodiments of the invention, the dotted line may be a double bond.

According to any embodiments of the invention, $R^2$ and $R^{2'}$ may be, independently from each other, a hydrogen atom, a methyl group, an ethyl group or a $CHR^1XH$ group, or $R^2$ and $R^{2'}$ when taken together form a carbonyl group. Particularly, $R^2$ and $R^{2'}$ may be, independently from each other, a hydrogen atom, a methyl group, an ethyl group, or a $CHR^1OH$ group, or $R^2$ and $R^{2'}$ when taken together form a carbonyl group. Particularly, $R^2$ and $R^{2'}$ may be, independently from each other, a methyl group, an ethyl group or a hydroxymethyl group, or $R^2$ and $R^{2'}$ when taken together form a carbonyl group. Particularly, $R^2$ may be a methyl group or an ethyl group and $R^{2'}$ may be a hydroxymethyl group, or $R^2$ and $R^{2'}$ when taken together form a carbonyl group Particularly, $R^2$ and $R^{2'}$ may be taken together and form a carbonyl group.

According to any embodiments of the invention, the invention's compound is of formula (V)

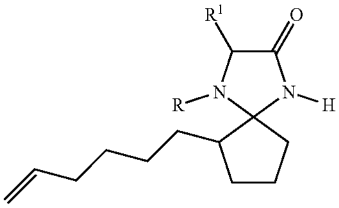

in the form of any one of its stereoisomers or as a mixture thereof, wherein R and $R^1$ have the same meaning as defined above.

According to any embodiments of the invention, $R^1$ may be a hydrogen atom or a $C_{1-4}$ alkyl group optionally substituted by an amide, a guanidine, a thiol, a primary amine (i.e. $NH_2$), a $C_{1-3}$ thioether, preferably a $SCH_3$, a phenyl, a hydroxyphenyl, a carboxylic acid, a hydroxy or a $C_{4-8}$ heterocycloalkenyl group, wherein the heteroatom is one or two nitrogen atoms, such as an imidazolyl or an indolyl group. In other words, $R^1$ may a hydrogen atom or a residue derived from an amino acid of formula $R^1CH(NH_2)COOH$, and in particular of a natural α-amino acid, such as S-alanine ($R^1$=$CH_3$), S-arginine [$R^1$=$(CH_2)_3NHC(NH)(NH_2)$], S-asparagine ($R^1$=$CH_2CONH_2$), R-cysteine ($R^1$=$CH_2SH$), S-glutamine [$R^1$=$(CH_2)_2CONH_2$], glycine ($R^1$=H), S-histidine ($R^1$=$CH_2C_3N_2H_3$), S-isoleucine [$R^1$=$C(CH_3)CH_2CH_3$], S-leucine [$R^1$=$CH_2CH(CH_3)_2$], S-lysine [$R^1$=$(CH_2)_4NH_2$], S-methionine [$R^1$=$(CH_2)_2SCH_3$], S-phenylalanine ($R^1$=$CH_2C_6H_5$), S-serine ($R^1$=$CH_2OH$), S-threonine [$R^1$=$CH(OH)CH_3$], S-tryptophane ($R^1$=$CH_2C_8H_6N$), S-tyrosine ($R^1$=$CH_2C_6H_4OH$), S-valine [$R^1$=$CH(CH_3)_2$], S-aspartic acid ($R^1$=$CH_2COOH$), and S-glutamic acid [$R^1$=$(CH_2)_2COOH$], or of an artificial α-amino acid selected from the group of norleucine [$R^1$=$(CH_2)_3CH_3$], norvaline [$R^1$=$(CH_2)_2CH_3$], 2-phenylglycine ($R^1$=$C_6H_5$), ornithine [$R^1$=$(CH_2)_3NH_2$], homoalanine ($R^1$=$CH_2CH_3$), homocysteine [$R^1$=$(CH_2)_2SH$], and homoserine [$R^1$=$(CH_2)_2OH$]. Particularly, $R^1$ may be a hydrogen atom, a methyl group, an ethyl group or a benzyl group. Even more particularly, $R^1$ may be a hydrogen atom, a methyl group or an ethyl group.

The term "heterocycloalkenyl" is understood as comprising 1, 2 or more olefinic double bonds, and as comprising monocyclic or fused, spiro and/or bridged bicyclic or tricyclic heterocycloalkenyl groups, preferably monocyclic or fused bicyclic heterocycloalkenyl groups.

According to a particular embodiment of the invention, R and $R^1$ may be taken together and form a $C_{4-5}$ azocycloalkyl group. Particularly, R and $R^1$ may be taken together and form a $C_4$ azocycloalkyl group.

According to any one of the above embodiments, said compound of formula (I) may be 6-(5-hexenyl)-1,4-diazaspiro[4.4]nonan-2-one, 2-(5-hexenyl)tetrahydrospiro[cyclopentane-1,3'-pyrrolo[1,2-c]imidazol]-1'(2'H)-one, 6-(hex-5-en-1-yl)-3-methyl-1,4-diazaspiro[4.4]nonan-2-one, 3-benzyl-6-(hex-5-en-1-yl)-1,4-diazaspiro[4.4]nonan-2-one, 2-(hex-5-en-1-yl)tetrahydro-2'H-spiro[cyclopentane-1,3'-imidazo[1,5-a]pyridin]-1'(5'H)-one, 6-pentyl-1,4-diazaspiro[4.4]nonan-2-one, 3-methyl-6-pentyl-1,4-diazaspiro[4.4]nonan-2-one, 3-benzyl-6-pentyl-1,4-diazaspiro[4.4]nonan-2-one, 2-pentyltetrahydrospiro[cyclopentane-1,3'-pyrrolo[1,2-c]imidazol]-1'(2'H)-one, 2-pentyltetrahydro-2'H-spiro[cyclopentane-1,3'-imidazo[1,5-a]pyridin]-1'(5'H)-one, 7-methyl-6-pentyl-1,4-diazaspiro[4.4]nonan-2-one, 6-hexyl-1,4-diazaspiro[4.4]nonan-2-one, 2-hexyltetrahydrospiro[cyclopentane-1,3'-pyrrolo[1,2-c]imidazol]-1'(2'H)-one, 6-heptyl-1,4-diazaspiro[4.4]nonan-2-one, 2-heptyltetrahydrospiro[cyclopentane-1,3'-pyrrolo[1,2-c]imidazol]-1'(2'H)-one, 6-(but-3-en-1-yl)-6,9,9-trimethyl-1,4-diazaspiro[4.4]nonan-2-one, methyl 2-(2-oxo-6-pentyl-1,4-diazaspiro[4.4]nonan-7-yl)acetate, (6-(hex-5-en-1-yl)-3-methyl-1-oxa-4-azaspiro[4.4]nonan-3-yl)methanol, (6-(hex-5-en-1-yl)-1-oxa-4-azaspiro[4.4]nonan-3-yl)methanol, (3-methyl-6-pentyl-1-oxa-4-azaspiro[4.4]nonan-3-yl)methanol, (6-pentyl-1-oxa-4-azaspiro[4.4]nonan-3-yl)methanol, (6-hexyl-3-methyl-1-oxa-4-azaspiro[4.4]nonan-3-yl)methanol, (6-hexyl-1-oxa-4-azaspiro[4.4]nonan-3-yl)methanol, (6-heptyl-3-methyl-1-oxa-4-azaspiro[4.4]nonan-3-yl)methanol or (6-heptyl-1-oxa-4-azaspiro[4.4]nonan-3-yl)methanol in the form of any one of its stereoisomers. Preferably, the compound of formula (I) may be 2-(5-hexenyl)tetrahydrospiro[cyclopentane-1,3'-pyrrolo[1,2-c]imidazol]-1'(2'H)-one or 2-pentyltetrahydrospiro[cyclopentane-1,3'-pyrrolo[1,2-c]imidazol]-1'(2'H)-one. Particularly, the compound of formula (I) may be 2-(5-hexenyl)tetrahydrospiro[cyclopentane-1,3'-pyrrolo[1,2-c]imidazol]-1'(2'H)-one.

The compounds according to formula (I) are able to slowly generate a cyclopentanone derivative of formula (VI) over time (VI)

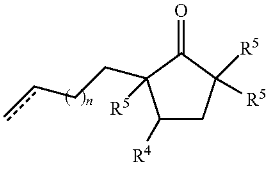

in the form of any one of its stereoisomers or as a mixture thereof, wherein the dotted line, n, $R^4$ and $R^5$ and have the same meaning as defined above.

The compounds of formula (I) are non-volatile and essentially odorless. At the same time, they are relatively stable in perfuming compositions or perfumed articles. When exposed to a surface under environmental conditions compounds (VI) are believed to be formed by reaction with ambient humidity. The generation of these compounds may further be triggered by the presence of oxygen in the air, by pH changes, by exposure to light, in particular to UV-A light, the presence of enzymes, or at increased temperature, or by other types of mechanisms, or by the combination of several mechanisms.

Non-volatile and essentially odorless compounds are advantageously characterized by a vapor pressure below 2.0 Pa, as obtained by calculation using the software EPIwin v. 3.10 (2000, available at the US Environmental Protection Agency). Preferably, said vapor pressure is below 0.2 Pa, or even more preferably below 0.02 Pa.

Although it is not possible to provide an exhaustive list of the compounds of formula (VI) which are generated from the invention's compound of formula (I), one can cite as preferred and non-limiting examples the following: 2-(5-hexen-1-yl)cyclopentanone, 2-hexyl-1-cyclopentanone, 2-heptyl-1-cyclopentanone, 2-pentyl-1-cyclopentanone, 2,2,5-trimethyl-5-pentyl-1-cyclopentanone, methyl 2-[3-oxo-2-pentylcyclopentyl]acetate, 3-methyl-2-pentylcyclopentan-1-one, methyl 3-oxo-2-pentylcyclopentane-1-carboxylate or 2-(3-buten-1-yl)-2,5,5-trimethylcyclopentanone. Particularly, the compound of formula (VI) may be 2-(5-hexen-1-yl)cyclopentanone.

As mentioned above, the invention concerns the use of a compound of formula (I) as perfuming ingredient to provide a long-lasting odor, in particular, an odor imparted by perfumery ingredients derived from cyclopentanone, to the environment. In other words, it concerns a method to confer, enhance, improve or modify the odor, in particular an odor imparted by perfumery ingredients derived from cyclopentanone (i.e. fruity and/or floral odor), of a perfuming composition or of a perfumed article, which method comprises adding to said composition or article an effective amount of at least one compound of formula (I). By "use of a compound of formula (I)", it has to be understood here also the use of any composition containing a compound of formula (I) and which can be advantageously employed in the perfumery industry.

By "perfuming ingredient" it is meant here a compound, which is used in a perfuming preparation or a composition to impart a hedonic effect. In other words, such perfuming ingredient, to be considered as being a perfuming one, must be recognized by a person skilled in the art as being able to impart or modify in a positive or pleasant way the odor of a composition, and not just as having an odor.

The expression "fruity and/or floral odor" or "fruity and/or floral note" should be understood as an odor reminding that of a floral, e.g. rosy, and fruity olfactive impression, in particular yellow fruit notes, such as for example apricot, peach notes, or fruity-floral notes such as exotic fruit notes.

For sake of clarity, a long-lasting effect is typically achieved if, after a certain time, e.g. after several hours or days, a given compound emits higher amounts of an odor into the environment than a reference compound providing the same type of odor. Thus, the expression "long-lasting odor" when referring to the compound of formula (I) of the invention should be understood as an increase of duration of the odor perception (release of compounds into the atmosphere providing a fruity and/or floral olfactive impression) as compared to that of the molecules alone that have such an impression, and measured under the same conditions for example after several hours (6 or 8 hours) or days (1, 3 or 7 days).

Said compositions, which in fact can be advantageously employed as perfuming ingredients, are also an object of the present invention.

Therefore, another aspect of the present invention is a perfuming composition comprising:

i) as perfuming ingredient, at least one invention's compound of formula (I) as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

A solid carrier is meant to designate a material to which the perfuming composition or some element of the perfuming composition can be chemically or physically bound. In general, such solid carriers are employed either to stabilize the composition, or to control the rate of evaporation of the compositions or of some ingredients. The use of a solid carrier is of current use in the art and a person skilled in the art knows how to reach the desired effect. However, by way of non-limiting examples of solid carriers, one may cite absorbing gums or polymers or inorganic material, such as porous polymers, cyclodextrins, wood-based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation techniques.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like a phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively, one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Other resins are those produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine-based resins with aldehydes is represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited, is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition in addition to the perfuming ingredient of formula (I), and imparting such as the perfuming ingredient of formula (I) a hedonic effect. In other words, such a co-ingredient, to be considered as being a perfuming one, must be recognized by a person skilled in the art as being able to impart or modify in a positive or pleasant way the odor of a composition, and not just as having an odor.

In particular, one may cite perfuming co-ingredients which are commonly used in perfume formulations, such as:

Aldehydic ingredients: decanal, dodecanal, 2-methyl-undecanal, 10-undecenal, octanal, nonanal and/or nonenal;

Aromatic-herbal ingredients: eucalyptus oil, camphor, eucalyptol, 5-methyltricyclo[6.2.1.0~2,7~]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;

Balsamic ingredients: coumarin, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dimethylethyl)-1-cyclohexyl acetate, verdyl isobutyrate and/or mixture of methylionones isomers;

Fruity ingredients: gamma-undecalactone, 2,2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate, 3-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl[3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, oxacyclohexadecan-2-one and/or (1S,1'R)-[1-(3',3'-dimethyl-1'-cyclohexyl)ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.$0^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds also known as properfumes or profragrances. Non-limiting examples of suitable properfumes or profragrances may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, 3-(dodecylthio)-1-(2,6,6-trimethyl-3-cyclohexen-1-yl)-1-butanone, 2-(dodecylthio)octan-4-one, 2-phenylethyl oxo(phenyl)acetate, 3,7-dimethylocta-2,6-dien-1-yl oxo(phenyl)acetate, (Z)-hex-3-en-1-yl oxo(phenyl)acetate, 3,7-dimethyl-2,6-octadien-1-yl hexadecanoate, bis(3,7-dimethylocta-2,6-dien-1-yl) succinate, (2-((2-methylundec-1-en-1-yl)oxy)ethyl)benzene, 1-methoxy-4-(3-methyl-4-phenethoxybut-3-en-1-yl)benzene, (3-methyl-4-phenethoxybut-3-en-1-yl)benzene, 1-(((Z)-hex-3-en-1-yl)oxy)-2-methylundec-1-ene, (2-((2-methylundec-i-en-1-yl)oxy)ethoxy)benzene, 2-methyl-1-(octan-3-yloxy)undec-1-ene, 1-methoxy-4-(1-phenethoxyprop-1-en-2-yl)benzene, 1-methyl-4-(1-phenethoxyprop-1-en-2-yl)benzene, 2-(1-phenethoxyprop-1-en-2-yl)naphthalene, (2-phenethoxyvinyl)benzene, 2-(1-((3,7-dimethyloct-6-en-1-yl)oxy)prop-1-en-2-yl)naphthalene, (2-((2-pentylcyclopentylidene)methoxy)ethyl)benzene or a mixture thereof.

The term "perfumery adjuvant" is understood as an ingredient capable of imparting additional added benefit such as a color, a particular light resistance, chemical stability etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above-mentioned components of a perfuming composition, simply by applying the standard knowledge of the art as well as by trial and error methodologies.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that is important to have the possibility, in the compositions mentioned above, to use in addition to a compound of formula (I) other compounds of similar or different nature being able to generate other fragrances, as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compound of formula (I) can also be advantageously used in all the fields of modem perfumery, i.e. fine or functional perfumery, to positively impart a long-lasting or substantive fruity and/or floral odor to a consumer product into which said compound (I) is added.

Consequently, another aspect of the present invention relates to a perfuming consumer product comprising as perfuming ingredient, at least one compound of formula (I) or a perfuming composition, as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

As used herein "consumer product" means baby care, personal care, fabric & home care, family care, feminine care, health care, beauty care and like products generally intended to be used or consumed in the form in which they are sold.

Non-limiting examples of suitable perfuming consumer products can be a perfume, such as a fine perfume, a cologne or an after-shave lotion; a fabric care product, such as a liquid or solid detergent or a unidose detergent (like a powder tablet, a liquid unidose or a multichamber unidose detergent), a fabric softener, a fabric refresher, an ironing water, a paper, a bleach, a carpet cleaner, or curtain-care product; a body-care product, such as a hair care product (e.g. a shampoo, a coloring preparation or a hair spray, a color care product or a hair shaping product), a dental care product, a disinfectant, an intimate care product), a cosmetic preparation (e.g. a skin cream or lotion, a vanishing cream or a deodorant or antiperspirant (e.g. a spray or roll on), a hair remover, a tanning, sun or after sun product, a nail product, a skin cleansing product or a makeup), a skin-care product (e.g. a perfumed soap, shower or bath mousse, oil or gel, a hygiene product or a foot/hand care product); an air care product, such as an air freshener or a "ready to use" powdered air freshener, which can be used in the home space (rooms, refrigerators, cupboards, shoes or car) and/or in a public space (halls, hotels, malls, etc.); or a home care product, such as a mold remover, a furnisher care product, a wipe, a dish detergent or hard-surface (e.g. a floor, bath, sanitary or a windows) detergent, a leather care product; a car care product, such as a polish, waxes or a plastic cleaner.

Preferred perfuming compositions or perfumed articles are perfumes, fabric or hard-surface detergents, skin or hair-care products and fabric softeners or refreshers.

Typical examples of fabric detergents or softener compositions into which the compounds of the invention can be incorporated are described in WO 97/34986, or in U.S. Pat. Nos. 4,137,180 and 5,236,615 or in EP 799 885. Other typical detergents and softening compositions which can be used are described in works such as Ullmann's Encyclopedia of Industrial Chemistry, vol. 20, Wiley-VCH, Weinheim, p. 355-540 (2012); Flick, Advanced Cleaning Product Formulations, Noye Publication, Park Ridge, New Jersey (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer products, typical concentrations are in the order of 0.0001% to 5% by weight, or even more, of the compounds of the invention based on the weight of the consumer product into which they are incorporated.

As mentioned above, the invention concerns a method of imparting a long-lasting or substantive odor imparted by perfumery ingredients derived from cyclopentanone, such as fruity and/or floral odors, to surfaces, such as hard surfaces, fabric, skin or hair. Perfume ingredients that provide a fruity and/or floral odor to the environment by evaporation from a surface are typically not very long-lasting or substantive. As outlined above, one reason for this is their relatively high volatility, which guarantees an efficient evaporation after surface deposition. Another reason for this is that quite often only small amounts of these compounds are efficiently deposited on the surface. This is, in particular, the case if they are applied to a surface via perfuming compositions or perfumed articles, which are rinsed after application. This rinsing step also carries away a large amount of the perfume, which is supposed to remain on the target surface. Examples for this case are washing and cleaning agents, such as hard surface cleaners, detergents, shower gels shampoos and the like, which are rinsed off after application. Furthermore, perfuming a surface by bringing it into contact with perfuming compositions or perfumed articles from which the perfume is deposited onto the surface by a partition equilibrium between the perfuming compositions or perfumed articles and the corresponding surface might be inefficient for the deposition of the perfume. Examples for this case are conditioners or surface refreshers, such as fragrance softeners, which are brought into contact with the target and then removed or left drying. Compounds of formula (I) according to the present invention are suitable to enhance the deposition of the perfume and thus to impart a long-lasting odor imparting by cyclopentanone-derivative-perfumery ingredients to surfaces, such as hard surfaces, fabric, skin or hair.

Therefore, another aspect of the present invention concerns a method of imparting a long-lasting or substantive odor imparted by perfumery ingredients derived from cyclopentanone to the environment or to surfaces, such as hard surfaces, fabric, skin or hair, by adding at least one compound of formula (I) to perfuming compositions or perfumed articles and applying them to the corresponding targeted environment or surface.

The present invention also relates to a microcapsule comprising at least one compound of formula (I). In one embodiment, the at least one compound of formula (I) is encapsulated in a core-shell microcapsule wherein the at least one compound of formula (I) is contained in the core surrounded by the shell. In one embodiment, the shell of the microcapsule protects the compound of formula (I) from the environment. The shell is made of material which is able to release the at least one compound of formula (I). In one embodiment, the shell is made of material which is able to release the compound of formula (I) upon breakage of the shell and/or by diffusion through the shell. A person skilled in the art is well aware of processes to prepare said microcapsules.

According to a particular embodiment, the shell of the microcapsule comprises a material selected from the group consisting of polyurea, polyurethane, polyamide, polyester, poly(meth)acrylate (i.e. polyacrylate and/or polymethacrylate), polysiloxane, polycarbonate, polysulfonamide, polymers of urea and formaldehyde, melamine and formaldehyde, melamine and urea, or melamine and glyoxal and mixtures thereof. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to a particular embodiment, the core-shell microcapsule(s) can be also derived by using different or more than one encapsulation method.

In a preferred embodiment, the shell of the microcapsules may be, each independently, selected from the group of aminoplast, polyamide, polyester, polyurea and polyurethane shells and mixtures thereof.

In a particular embodiment, the shell of the microcapsules comprises an aminoplast copolymer, such as melamine-formaldehyde or urea-formaldehyde or cross-linked melamine formaldehyde or melamine glyoxal.

In a particular embodiment, the shell of the microcapsules is polyurea-based made from, for example but not limited to, isocyanate-based monomers and amine-containing cross-linkers such as guanidine carbonate and/or guanazole. Certain polyurea microcapsules comprise a polyurea wall which is the reaction product of the polymerization between at least one polyisocyanate comprising at least two isocyanate functional groups and at least one reactant selected from the group consisting of an amine (for example a water-soluble guanidine salt and guanidine); a colloidal stabilizer or emulsifier; and an encapsulated perfume. However, the use of an amine can be omitted.

In a particular embodiment, the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). In a particular embodiment, the emulsifier is an anionic or amphiphilic biopolymer, which may be for example chosen from the group consisting of gum Arabic, soy protein, gelatin, sodium caseinate and mixtures thereof.

In a particular embodiment, the shell of the microcapsules is polyurethane-based made from, for example but not limited to, polyisocyanate and polyols, polyamide, polyester, etc.

In a particular embodiment, the microcapsules have a polymeric shell resulting from complex coacervation wherein the shell is possibly cross-linked.

In a particular embodiment of the core-shell microcapsules, the core-shell microcapsules comprise an oil-based core comprising a hydrophobic active, preferably at least one compound of formula (I), and a composite shell comprising a first material and a second material, wherein the first material and the second material are different, the first material is a coacervate, the second material is a polymeric material.

In a particular embodiment, the weight ratio between the first material and the second material is comprised between 50:50 and 99.9:0.1.

In a particular embodiment, the coacervate comprises a first polyelectrolyte, preferably selected among proteins (such as gelatin), polypeptides or polysaccharides (such as chitosan), most preferably gelatin, and a second polyelectrolyte, preferably alginate salts, cellulose derivatives, guar gum, pectinate salts, carrageenan, polyacrylic and methacrylic acid or xanthan gum, or yet plant gums such as acacia gum (Gum Arabic), most preferably Gum Arabic.

The first coacervate material can be hardened chemically using a suitable cross-linker such as glutaraldehyde, glyoxal, formaldehyde, tannic acid or genipin or can be hardened enzymatically using an enzyme such as transglutaminase.

The second polymeric material can be selected from the group consisting of polyurea, polyurethane, polyamide, polyester, polyacrylate, polysiloxane, polycarbonate, polysulfonamide, polymers of urea and formaldehyde, melamine and formaldehyde, melamine and urea, or melamine and glyoxal and mixtures thereof, preferably polyurea and/or polyurethane. The second material is preferably present in an amount less than 3 wt. %, preferably less than 1 wt. % based on the total weight of the microcapsule slurry.

The preparation of an aqueous dispersion/slurry of core-shell microcapsules is well known by a skilled person in the art. In a particular embodiment, the microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable urea include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

In a particular embodiment of the core-shell microcapsules, the core-shell microcapsules comprise

- an oil-based core comprising a hydrophobic active, preferably comprising at least one compound of formula (I),
- optionally an inner shell made of a polymerized polyfunctional monomer;
- a biopolymer shell comprising a protein, wherein at least one protein is cross-linked.

According to a particular embodiment, the protein is chosen from the group consisting of milk proteins, caseinate salts such as sodium caseinate or calcium caseinate, casein, whey protein, hydrolyzed proteins, gelatins, gluten, pea protein, soy protein, silk protein and mixtures thereof, preferably sodium caseinate, most preferably sodium caseinate.

According to a particular embodiment, the protein comprises sodium caseinate and a globular protein, preferably chosen from the group consisting of whey protein, beta-lactoglobulin, ovalbumine, bovine serum albumin, vegetable proteins, and mixtures thereof.

The protein is preferably a mixture of sodium caseinate and whey protein.

According to a particular embodiment, the biopolymer shell comprises a crosslinked protein chosen from the group consisting of sodium caseinate and/or whey protein.

According to a particular embodiment, the microcapsule slurry comprises at least one microcapsule made of:

- an oil-based core comprising the hydrophobic active, preferably comprising at least one compound of formula (I);

an inner shell made of a polymerized polyfunctional monomer; preferably a polyisocyanate having at least two isocyanate functional groups;

a biopolymer shell comprising a protein, wherein at least one protein is cross-linked; wherein the protein contains preferably a mixture comprising sodium caseinate and a globular protein, preferably whey protein;

optionally at least an outer mineral layer.

According to an embodiment, sodium caseinate and/or whey protein is (are) cross-linked protein(s).

The weight ratio between sodium caseinate and whey protein is preferably comprised between 0.01 and 100, preferably between 0.1 and 10, more preferably between 0.2 and 5.

In a particular embodiment, the microcapsule is a one-shell aminoplast core-shell microcapsule obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) preparing an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain the dried core-shell microcapsule.

In a particular embodiment, the core-shell microcapsule is a formaldehyde-free capsule. A typical process for the preparation of an aminoplast formaldehyde-free microcapsule slurry comprises the steps of 1) preparing an oligomeric composition comprising the reaction product of, or obtainable by reacting together:
   a. a polyamine component in the form of melamine or of a mixture of melamine and at least one $C_1$-$C_4$ compound comprising two $NH_2$ functional groups;
   b. an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c. a protic acid catalyst;
2) preparing an oil-in-water dispersion, wherein the droplet size is comprised between 1 and 600 microns, and comprising:
   a. an oil;
   b. a water medium;
   c. at least an oligomeric composition as obtained in step 1;
   d. at least a cross-linker selected amongst:
      i. $C_4$-$C_{12}$ aromatic or aliphatic di- or tri-isocyanates and their biurets, triurets, trimmers, trimethylol propane-adduct and mixtures thereof; and/or
      ii. a di- or tri-oxiran compound of formula:

Q-(oxiran-2-ylmethyl)$_m$ wherein m is 2 or 3 and Q represents a $C_2$-$C_6$ group optionally comprising from 2 to 6 nitrogen and/or oxygen atoms;
   e. optionally a $C_1$-$C_4$ compounds comprising two $NH_2$ functional groups;
3) heating the dispersion; and
4) cooling the dispersion.

The above process is described in more detail in WO 2013/068255.

In a particular embodiment of the core-shell microcapsules, the core-shell microcapsule is a polyamide core-shell microcapsule comprising:

an oil based core comprising an hydrophobic active, preferably comprising at least one compound of formula (I), and a polyamide shell comprising or being obtainable from:
   an acyl chloride,
   a first amino compound, and
   a second amino compound.

According to a particular embodiment, the polyamide core-shell microcapsule comprises:

an oil based core comprising an hydrophobic active, preferably comprising at least one compound of formula (I), and a polyamide shell comprising or being obtainable from:
   an acyl chloride, preferably in an amount comprised between 5 and 98%, preferably between 20 and 98%, more preferably between 30 and 85% w/w;
   a first amino compound, preferably in an amount comprised between 1% and 50% w/w, preferably between 7 and 40% w/w;
   a second amino compound, preferably in an amount comprised between 1% and 50% w/w, preferably between 2 and 25% w/w;
   a stabilizer, preferably a biopolymer, preferably in an amount comprised between 0 and 90%, preferably between 0.1 and 75%, more preferably between 1 and 70%.

According to a particular embodiment, the polyamide core-shell microcapsule comprises:

an oil based core comprising a hydrophobic active, preferably comprising at least one compound of formula (I), and a polyamide shell comprising or being obtainable from:
   an acyl chloride,
   a first amino-compound being an amino-acid, preferably chosen from the group consisting of L-Lysine, L-Arginine, L-Histidine, L-Tryptophane and/or a mixture thereof.
   a second amino.compound chosen from the group consisting of ethylene diamine, diethylene triamine, cystamine and/or a mixture thereof, and
   a biopolymer chosen from the group consisting of casein, sodium caseinate, bovin serum albumin, whey protein, and/or a mixture thereof.

The first amino-compound can be different from the second amino-compound. Typically, a process for preparing a polyamide-based microcapsule includes the following steps:

a) Dissolving at least one acyl chloride in a hydrophobic material, preferably a perfume to form an oil phase;
b) Dispersing the oil phase obtained in step a) into a water phase comprising a first amino compound to form an oil-in water emulsion;
c) Performing a curing step to form polyamide microcapsules in the form of a slurry; wherein a stabilizer is added in the oil phase and/or in the water phase, and wherein at least a second amino-compound is added in the water phase before the formation of the oil-in-water emulsion and/or in the oil-in water emulsion obtained after step b).

In a particular embodiment, the shell of the microcapsule is polyurea- or polyurethane-based. Examples of processes for the preparation of polyurea and polyureathane-based microcapsule slurries are for instance described in WO 2007/004166, EP 2300146, and EP 2579976. Typically a process for the preparation of polyurea or polyurethane-based microcapsule slurries include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and 50 μm; and
d) Applying conditions sufficient to induce interfacial polymerization and form microcapsules in form of a slurry.

In a particular embodiment, the microcapsule can be in form of a powder, which in particular may be obtained by submitting the microcapsule slurry to a drying step, like spray-drying, to provide the microcapsules as such, i.e. in a powdery form. It is understood that any standard method known by a person skilled in the art to perform such drying is also applicable. In particular the slurry may be spray-dried, preferably in the presence of a polymeric carrier material such as polyvinyl acetate, polyvinyl alcohol, dextrins, natural or modified starch, gum Arabic, vegetable gums, pectins, xanthans, alginates, carrageenans or cellulose derivatives to provide microcapsules in a powder form.

However, one may cite also other drying methods such as extrusion, plating, spray granulation or fluidized bed processes, or even a drying at room temperature using materials (carrier, desiccant) that meet specific criteria as disclosed in WO 2017/134179.

The invention's compounds of formula (I) can be prepared according to standard methods known in the art as described herein-below.

EXAMPLES

The invention is hereafter described in a more detailed manner by way of the following examples, wherein the abbreviations have the usual meaning in the art, temperatures are indicated in degrees centigrade (° C.). NMR spectral data were recorded on a Bruker Avance III 500 or 600 spectrometer. If not indicated otherwise, the spectra were recorded in $CDCl_3$ at 500 MHz for $^1H$ and at 125.8 MHz for $^{13}C$. The chemical displacements δ are indicated in ppm with respect to $Si(CH_3)_4$ as the standard, the coupling constants J are expressed in Hz (br.=broad peak). Reactions were carried out in standard glassware under $N_2$. Commercially available reagents and solvents were used without further purification if not stated otherwise.

Although specific conformations or configurations are indicated for some of the compounds, this is not meant to limit the use of these compounds to the isomers described.

Example 1

Preparation of Compounds According to Formula (I)

(a) Synthesis of (±)-6-(5-hexenyl)-1,4-diazaspiro[4.4]nonan-2-one (Compound 1)

In a soxhlet extractor with molecular sieves (4 Å), a mixture of 2-(5-hexenyl)cyclopentan-1-one (1.73 g, 10 mmol), triethylamine (TEA, 1.5 mL, 11 mmol) and glycinamide hydrochloride (1.13 g, 10 mmol) in methanol (125 mL) was heated under reflux for several days. After cooling to room temperature, the solvent was evaporated under reduced pressure and the mixture taken up in ethyl acetate (50 mL) and water (25 mL). After separation, the aqueous phase was re-extracted with ethyl acetate (50 mL) and the organic phases washed with a saturated aqueous solution of NaCl (25 mL). The combined organic phases were dried ($Na_2SO_4$), filtered and concentrated under reduced pressure. Column chromatography ($SiO_2$, ethyl acetate) afforded 0.15 g of the first diastereoisomer (Compound 1a) of the target product; further elution (ethyl acetate/ethanol) yielded 0.24 g of a mixture of isomers and 0.19 g of the second diastereoisomer (Compound 1b). The compound can be used in the form of its individual separated diastereoisomers or as the non-separated mixture of isomers.

$^1H$-NMR (Compound 1a): 6.89 (br. s, 1H), 5.85-5.74 (m, 1H), 5.03-4.91 (m, 2H), 3.50 (d, J=16.4, 1H), 3.41 (d, J=16.4, 1H), 2.09-2.00 (m, 2H), 1.97-1.84 (m, 3H), 1.83-1.58 (m, 4H), 1.56-1.46 (m, 1H), 1.45-1.33 (m, 4H), 1.31-1.17 (m, 2H).

$^{13}C$-NMR (Compound 1a): 176.76, 138.86, 114.41, 85.22, 49.72, 48.72, 39.34, 33.65, 29.17, 28.39, 28.08, 27.86, 19.79.

$^1H$-NMR (Compound 1b): 7.43 (br. s, 1H), 5.85-5.74 (m, 1H), 5.03-4.91 (m, 2H), 3.49 (m, 2H), 2.09-1.94 (m, 4H), 1.91-1.79 (m, 2H), 1.78-1.64 (m, 3H), 1.53-1.19 (m, 6H), 1.18-1.09 (m, 1H).

$^{13}C$-NMR (Compound 1b): 176.73, 138.82, 114.43, 86.18, 49.29, 48.98, 39.59, 33.67, 29.53, 29.43, 29.09, 27.76, 20.51.

(b) Synthesis of (±)-(7a'S)-2-(5-hexenyl)tetrahydrospiro[cyclopentane-1,3'-pyrrolo[1,2-c]imidazol]-1'(2'H)-one (Compound 2)

As described for Compound 1 with 2-(5-hexenyl)cyclopentan-1-one (1.73 g, 10 mmol), TEA (2.25 mL, 16 mmol), L-prolinamide hydrochloride (2.26 g, 15 mmol) in methanol (125 mL). Column chromatography ($SiO_2$, ethyl acetate, then ethyl acetate/ethanol 9:1) afforded several product fractions, which were re-purified ($SiO_2$, ethyl acetate) to give 0.22 g of the first diastereoisomer (Compound 2a) and 0.48 g of the second diastereoisomer of the target product (Compound 2b). The compound can be used in the form of its individual separated diastereoisomers or as the non-separated mixture of isomers.

$^1H$-NMR (Compound 2a, 600 MHz): 6.85 (br. s, 1H), 5.84-5.74 (m, 1H), 5.03-4.89 (m, 2H), 3.78 (dd, J=9.6, 5.8, 1H), 2.95-2.88 (m, 1H), 2.75-2.67 (m, 1H), 2.18-1.95 (m, 4H), 1.94-1.86 (m, 1H), 1.86-1.62 (m, 7H), 1.62-1.54 (m, 1H), 1.51-1.43 (m, 1H), 1.43-1.30 (m, 3H), 1.24-1.14 (m, 2H).

$^{13}C$-NMR (Compound 2a, 151.0 MHz): 178.94, 139.01, 114.26, 87.00, 65.01, 51.76, 50.35, 33.75, 32.16, 29.45, 29.22, 27.80, 27.59, 27.05, 25.61, 19.84.

$^1H$-NMR (Compound 2b, 600 MHz): 7.32 (br. s, 1H), 5.82-5.73 (m, 1H), 5.01-4.89 (m, 2H), 3.92 (dd, J=9.2, 5.8, 1H), 3.06-2.99 (m, 1H), 2.77-2.69 (m, 1H), 2.18-2.10 (m, 1H), 2.10-1.99 (m, 3H), 1.99-1.88 (m, 3H), 1.86-1.66 (m, 5H), 1.59-1.50 (m, 1H), 1.43-1.30 (m, 3H), 1.30-1.18 (m, 2H), 1.14-1.05 (m, 1H).

$^{13}C$-NMR (Compound 2b, 151.0 MHz): 179.09, 138.90, 114.32, 87.58, 64.73, 50.83, 50.61, 33.76, 33.22, 29.72, 29.24, 27.71, 27.63, 27.17, 25.54, 20.11.

(c) Synthesis of (±)-(6-(hex-5-enyl)-3-methyl-1-oxa-4-azaspiro[4.4]nonan-3-yl)methanol (Compound 3)

2-Amino-2-methylpropane-1,3-diol (1.06 g, 10 mmol) and p-toluenesulfonic acid monohydrate (0.10 g) were added to a stirred solution of 2-(5-hexenyl)cyclopentan-1-one (3.82 g, 22 mmol) in toluene (25 mL). The mixture was heated under reflux overnight and, after cooling to room temperature, filtered over $NaHCO_3$ and concentrated. Column chromatography ($SiO_2$, n-heptane/ethyl acetate 7:3) afforded 1.21 g (48%) of a mixture of two pairs of diastereoisomers in a ratio of about 2:1.

$^1$H-NMR (major isomers): 5.86-5.75 (m, 1H), 5.03-4.90 (m, 2H), 3.70 and 3.69 (d, J=8.7, 1H), 3.53 and 3.43 (d, J=8.3, 1H), 3.44 and 3.31 (d, J=10.6, 1H), 3.41 (d, J=8.6, 1H), 2.34-0.98 (m, 15H), 1.27 and 1.24 (s, 3H), signals for OH and NH are not assigned.

$^{13}$C-NMR (major isomers): 139.13 and 138.96, 114.36 and 114.20, 105.35 and 105.14, 73.56 and 72.92, 66.71 and 66.43, 62.53 and 61.72, 47.97 and 47.81, 39.98 and 39.21, 33.79 and 33.75, 29.63, 29.28, 29.22, 29.16, 28.12, 28.00, 27.97, 27.90, 23.30 and 22.59, 21.33 and 20.81.

$^1$H-NMR (minor isomers): 5.86-5.75 (m, 1H), 5.03-4.90 (m, 2H), 3.70 and 3.66 (d, J=8.7, 1H), 3.49 and 3.47 (d, J=8.3, 1H), 3.46 and 3.34 (d, J=10.6, 1H), 3.39 and 3.33 (d, J=8.6, 1H), 2.34-0.98 (m, 15H), 1.26 (2 s, 3H), signals for OH and NH are not assigned.

$^{13}$C-NMR (minor isomers): 139.06 and 138.96, 114.41 and 114.26, 106.30 and 105.80, 72.92 and 72.49, 66.97 and 66.68, 62.97 and 62.38, 47.13 and 47.07, 38.19 and 37.79, 33.78 and 33.70, 30.64 and 29.93, 29.12 and 29.11, 28.99 and 28.96, 27.73 and 27.56, 23.30 and 22.93, 20.71 and 20.39.

(d) Synthesis of (±)-6-pentyl-1,4-diazaspiro[4.4]nonan-2-one (Compound 4)

A mixture of 2-pentylcyclopentan-1-one (13.90 g, 90 mmol), TEA (15 mL, 108 mmol) and glycinamide hydrochloride (10.15 g, 90 mmol) in methanol (250 mL) was heated under reflux for 16 h. After cooling to room temperature, the solvent was evaporated under reduced pressure. Water (50 mL) was added and the mixture extracted with ethyl acetate (2×100 mL). The combined organic phases were washed with a saturated aqueous solution of NaCl (50 mL), dried ($Na_2SO_4$), filtered and concentrated under reduced pressure. Column chromatography ($SiO_2$, n-heptane/ethyl acetate 7:3, then ethyl acetate/ethanol 1:1) afforded 6.75 g (36%) of a mixture of two diastereoisomers in a ratio of ca. 1:1.

$^1$H-NMR: 7.89 and 7.43 (br. s, 1H), 3.51 and 3.50 (d, J=16.4, 1H), 3.47 and 3.41 (d, J=16.4, 1H), 2.55-2.36 (br. m, 1H), 2.06-1.60 (m, 6H), 1.53-1.08 (m, 9H), 0.88 (t, J=6.8, 3H).

$^{13}$C-NMR: 177.08 and 176.94, 86.39 and 85.40, 49.83 and 49.36, 49.04 and 48.65, 39.61 and 39.29, 32.17 and 32.10, 29.60 and 28.21, 29.41 and 28.42, 28.07 and 28.00, 22.62 and 22.59, 20.53 and 19.81, 14.06.

(e) Synthesis of (±)-(3S)-3-methyl-6-pentyl-1,4-diazaspiro[4.4]nonan-2-one (Compound 5)

TEA (15.3 mL, 110 mmol) and 2-pentylcyclopentan-1-one (7.71 g, 50 mmol) were added to a solution of L-alaninamide hydrochloride (12.45 g, 100 mmol) in methanol (250 mL). The reaction mixture was heated under reflux for 24 h. After cooling to room temperature, the solvent was evaporated under reduced pressure. Water (100 mL) was added and the mixture extracted with ethyl acetate (100 mL). After phase separation, the aqueous phase was re-extracted with ethyl acetate (150 mL). The combined organic phases were washed with water (100 mL), a saturated aqueous solution of NaCl (100 mL), dried ($Na_2SO_4$), filtered and concentrated under reduced pressure to afford 8.23 g of a mixture of four diastereoisomers in a ratio of ca. 1.9:1.0:1.4:1.8 (Compound 5). Column chromatography of 6.18 g ($SiO_2$, ethyl acetate/n-heptane 4:1, then ethyl acetate) afforded 0.52 g of Compound 5a, 3.40 g of a mixture of Compounds 5a-5d and 0.13 g of Compound 5d. The compound can be used in the form of its individual separated diastereoisomers or as the non-separated mixture of isomers.

$^1$H-NMR (Compound 5a): 7.16 (br. s, 1H), 3.54 (q, J=6.9 Hz, 1H), 2.12-1.99 (m, 2H), 1.93-1.83 (m, 1H), 1.79-1.53 (m, 4H), 1.52-1.15 (m, 9H), 1.35 (d, J=7.1 Hz, 3H), 0.87 (t, J=7.1 Hz, 3H).

$^{13}$C-NMR (Compound 5a): 178.86, 83.13, 55.86, 49.83, 40.96, 32.21, 28.47, 28.41, 28.10, 22.59, 19.76, 18.52, 14.06.

$^1$H-NMR (Compound 5b, 600 MHz): 7.18 (br. s, 1H), 3.61 (q, J=6.8 Hz, 1H), 2.08-1.92 (m, 3H), 1.92-1.61 (m, 4H), 1.49-1.18 (m, 8H), 1.34 (d, J=6.9 Hz, 3H), 1.15-1.05 (m, 1H), 0.89 (t, J=6.9 Hz, 3H).

$^{13}$C-NMR (Compound 5b, 151.0 MHz): 178.83, 82.96, 54.24, 46.13, 38.51, 32.11, 28.47, 28.24, 27.93, 22.57, 19.73, 17.06, 14.05.

$^1$H-NMR (Compound 5c, 600 MHz): 7.61 (br. s, 1H); 3.64 (q, J=6.9 Hz, 1H), 2.08-1.92 (m, 2H), 1.92-1.61 (m, 5H), 1.49-1.18 (m, 8H), 1.34 (d, J=6.9 Hz, 3H), 1.15-1.05 (m, 1H), 0.87 (t, J=7.1 Hz, 3H).

$^{13}$C-NMR (Compound 5c, 151.0 MHz): 178.79, 84.06, 55.02, 49.42, 40.67, 32.14, 29.55, 28.00, 22.62, 20.29, 18.65, 14.05.

$^1$H-NMR (Compound 5d): 7.28 (br. s, 1H), 3.59 (q, J=6.8 Hz, 1H), 2.01-1.96 (m, 1H), 1.94-1.83 (m, 2H), 1.83-1.75 (m, 1H), 1.75-1.59 (m, 3H), 1.49-1.18 (m, 8H), 1.34 (d, J=7.1 Hz, 3H), 1.14-1.03 (m, 1H), 0.89 (t, J=6.9 Hz, 3H).

$^{13}$C-NMR (Compound 5d): 178.53, 83.71, 54.27, 48.29, 39.93, 32.11, 29.71, 29.66, 27.97, 22.61, 20.93, 17.48, 14.05.

(f) Synthesis of (±)-(3S)-3-benzyl-6-pentyl-1,4-diazaspiro[4.4]nonan-2-one (Compound 6)

A mixture of 2-pentylcyclopentan-1-one (3.87 g, 25 mmol), TEA (3.9 mL, 28 mmol) and L-phenylalaninamide hydrochloride (5.14 g, 25 mmol) in methanol (150 mL) was heated under reflux over the weekend. After cooling to room temperature, the solvent was evaporated under reduced pressure. Water (50 mL) was added and the mixture extracted with ethyl acetate (2×100 mL). The combined organic phases were washed with a saturated aqueous solution of NaCl (2×50 mL), dried ($Na_2SO_4$), filtered and concentrated under reduced pressure. Column chromatography ($SiO_2$, n-heptane/ethyl acetate 7:3, ethyl acetate and ethyl acetate/ethanol 1:1) afforded 1.01 g of a mixture of two diastereoisomers in a ratio of ca. 2.9:1 (Compound 6a) and 2.02 g of another mixture of two diastereoisomers in a ratio of ca. 1.2:1 (Compound 6b).

$^1$H-NMR (Compound 6a, major isomer): 7.34-7.19 (m, 5H), 7.04 (br. s, 1H), 3.80 (t, J=5.4 Hz, 1H), 3.07 (t, J=5.1, 2H), 2.08 (br. s, 1H), 1.88-1.72 (m, 2H), 1.72-1.50 (m, 3H), 1.50-1.38 (m, 1H), 1.38-1.03 (m, 9H), 0.87 (t, J=7.0 Hz, 3H).

$^{13}$C-NMR (Compound 6a, major isomer): 177.15, 136.87, 129.65, 128.63, 126.85, 83.22, 60.84, 49.75, 40.47, 37.49, 32.21, 28.36, 28.26, 28.06, 22.61, 19.64, 14.06.

$^1$H-NMR (Compound 6a, minor isomer): 7.47 (br. s 1H), 7.34-7.19 (m, 5H), 3.88 (dd, J=7.1, 4.2 Hz, 1H), 3.07 (dd, J=34.0, 5.1 Hz, 1H), 2.95 (dd, J=14.1, 7.1 Hz, 1H), 2.08 (br.

s, 1H), 2.00-1.89 (m, 1H), 1.88-1.72 (m, 1H), 1.72-1.50 (m, 4H), 1.50-1.38 (m, 2H), 1.38-1.03 (m, 7H), 0.86 (t, J=6.9 Hz, 3H).

$^{13}$C-NMR (Compound 6a, minor isomer): 176.96, 137.34, 129.64, 128.57, 126.76, 84.28, 60.38, 49.66, 40.54, 38.27, 32.14, 29.30, 28.93, 28.06, 22.64, 20.03, 14.04.

$^{1}$H-NMR (Compound 6b, major isomer): 7.34-7.21 (m, 5H), 3.82 (q, J=5.3 Hz, 1H), 3.12 (dd, J=14.1, 5.4 Hz, 1H), 3.06 (dd, J=13.3, 4.6 Hz, 1H), 2.20 (br. s, 1H), 1.99-1.74 (m, 3H), 1.74-1.51 (m, 2H), 1.50-1.40 (m, 1H), 1.37-0.96 (m, 7H), 0.91-0.70 (m, 2H), 0.87 (t, J=7.2 Hz, 3H), one signal for NH not assigned.

$^{13}$C-NMR (Compound 6b, major isomer): 177.06, 136.74, 129.79, 128.67, 126.96, 83.72, 59.33, 47.90, 40.39, 36.35, 31.86, 29.63, 28.98, 27.78, 22.50, 20.84, 14.06.

$^{1}$H-NMR (Compound 6b, minor isomer): 7.34-7.21 (m, 5H), 6.80 (br. s, 1H), 3.82 (q, J=5.3 Hz, 1H), 3.20 (dd, J=13.8, 5.2 Hz, 1H), 3.04 (dd, J=12.5, 4.8 Hz, 1H), 2.20 (br. s, 1H), 1.99-1.82 (m, 2H), 1.74-1.51 (m, 4H), 1.37-0.96 (m, 7H), 0.91-0.70 (m, 1H), 086 (t, J=7.3 Hz, 3H), 0.64-0.53 (m, 1H).

$^{13}$C-NMR (Compound 6b, minor isomer): 177.23, 136.67, 129.94, 128.70, 126.99, 82.85, 59.04, 46.43, 38.68, 35.78, 32.04, 28.41, 27.91, 27.37, 22.45, 19.67, 14.04.

(g) Synthesis of (±)-(7a'S)-2-pentyltetrahydrospiro [cyclopentane-1,3'-pyrrolo[1,2-c]imidazol]-1'(2'H)-one (Compound 7)

A mixture of 2-pentylcyclopentan-1-one (23.14 g, 150 mmol), TEA (46 mL, 330 mmol) and L-prolinamide hydrochloride (47.56 g, 300 mmol, 2 eq.) in methanol (500 mL) was heated under reflux for 22 h. After cooling to room temperature, the solvent was evaporated under reduced pressure. Water (150 mL) and pentane (150 mL) were added and the mixture was stirred for 15 min. After phase separation, the aqueous layer was re-extracted with pentane (2×150 mL) and the combined organic layers were washed with water (100 mL), dried ($Na_2SO_4$), filtered and concentrated. The residue was taken up in ethyl acetate, filtered through Celite® and activated charcoal, concentrated and dried under vacuum to afford 21.85 g (58%) of a mixture of three diastereoisomers in a ratio of ca. 9:6:1 (Compound 7). Column chromatography ($SiO_2$, ethyl acetate/n-heptane 2:1) allowed separation of the different isomers. The compound can be used in the form of its individual separated diastereoisomers or as the non-separated mixture of isomers.

$^{1}$H-NMR (Compound 7a): 7.41 (br. s, 1H), 3.93 (dd, J=9.3, 5.8 Hz, 1H), 3.07-2.99 (m, 1H), 2.77-2.72 (m, 1H), 2.19-2.01 (m, 2H), 2.01-1.87 (m, 3H), 1.87-1.61 (m, 5H), 1.59-1.48 (m, 1H), 1.39-1.14 (m, 7H), 1.13-1.03 (m, 1H), 0.86 (t, J=7.1 Hz, 3H).

$^{13}$C-NMR (Compound 7a): 179.15, 87.64, 64.73, 50.86, 50.60, 33.24, 32.24, 29.83, 27.91, 27.65, 27.14, 25.52, 22.68, 20.12, 14.07.

$^{1}$H-NMR (Compound 7b): 6.96 (br. s, 1H), 3.79 (dd, J=9.3, 5.4 Hz, 1H), 2.95-2.88 (m, 1H), 2.76-2.67 (m, 1H), 2.15-2.03 (m, 2H), 1.95-1.62 (m, 8H), 1.61-1.52 (m, 1H), 1.52-1.42 (m, 1H), 1.39-1.12 (m, 7H), 0.87 (t, J=6.9 Hz, 3H).

$^{13}$C-NMR (Compound 7b): 179.03, 87.03, 65.05, 51.81, 50.36, 32.23, 32.18, 29.55, 27.99, 27.59, 27.06, 25.61, 22.67, 19.84, 14.09.

$^{1}$H-NMR (Compound 7c): 6.74 (br. s, 1H), 3.85 (dd, J=9.6, 4.8 Hz, 1H), 3.04-2.95 (m, 1H), 2.64-2.55 (m, 1H), 2.19-2.04 (m, 3H), 2.04-1.94 (m, 2H), 1.91-1.53 (m, 5H), 1.51-1.05 (m, 9H), 0.89 (t, J=6.7 Hz, 3H).

$^{13}$C-NMR (Compound 7c): 179.21, 86.64, 63.68, 48.17, 42.77, 40.27, 31.87, 31.50, 30.76, 27.87, 25.69, 25.30, 22.60, 21.68, 14.06.

(h) Synthesis of (±)-2-pentyltetrahydro-2'H-spiro [cyclopentane-1,3'-imidazo[1,5-a]pyridin]-1'(5'H)-one (Compound 8)

TEA (0.85 mL, 6 mmol) and 2-pentylcyclopentan-1-one (4.63 g, 30 mmol) were added to a solution of 2-piperidinecarboxamide (8.09 g, 60 mmol) in methanol (50 mL). The reaction mixture was heated under reflux for 45 h and, after cooling to room temperature, concentrated. The residue was taken up in ethyl acetate (150 mL) and treated with water (50 mL). The aqueous phase was extracted with ethyl acetate (150 mL), and the combined organic phases were washed with water (50 mL) and a saturated aqueous solution of NaCl (50 mL), dried ($Na_2SO_4$), filtered and concentrated. Bulb-to-bulb distillation (130° C., 0.4 mbar) to remove the remaining 2-pentylcyclopentan-1-one yielded 3.14 g (40%) of a mixture of three diastereoisomers in a ratio of ca. 7:1:2 (Compound 8). Column chromatography ($SiO_2$, toluene/ethyl acetate 4:1, then 3:1) allowed (partial) separation of the different isomers, yielding Compound 8a, a mixture of Compounds 8a and 8b in a ratio of ca. 1:1.3 and Compound 8c. The compound can be used in the form of its individual separated diastereoisomers or as the non-separated mixture of isomers.

$^{1}$H-NMR (Compound 8a, 600 MHz): 6.93 (br. s, 1H), 2.88-2.81 (m, 2H), 2.27 (dt, J=11.0, 2.3 Hz, 1H), 2.02-1.82 (m, 4H), 1.77-1.43 (m, 7H), 1.39-1.11 (m, 9H), 1.03-0.94 (m, 1H), 0.88 (t, J=6.9 Hz, 3H).

$^{13}$C-NMR (Compound 8a, 151.0 MHz): 174.97, 86.01, 61.94, 44.48, 43.09, 32.09, 29.26, 29.00, 28.67, 28.15, 26.47, 25.57, 24.46, 22.63, 20.52, 14.10.

$^{1}$H-NMR (Compound 8b, 600 MHz): 6.45 (br. s, 1H), 2.89-2.81 (m, 1H), 2.81-2.75 (m, 1H), 2.38 (dt, J=10.9, 2.7 Hz, 1H), 2.24-2.14 (m, 1H), 2.03-1.82 (m, 3H), 1.82-1.10 (m, 17H), 0.88 (t, J=6.9 Hz, 3H).

$^{13}$C-NMR (Compound 8b, 151.0 MHz): 174.91, 85.04, 62.21, 48.20, 47.35, 32.29, 30.90, 30.28, 29.27, 28.22, 26.36, 25.20, 24.15, 22.67, 21.46, 14.13.

$^{1}$H-NMR (Compound 8c, 600 MHz): 6.94 (br. s, 1H), 3.31-3.24 (m, 1H), 3.00-2.93 (m, 1H), 2.52 (dt, J=11.6, 2.7 Hz, 1H), 2.01-1.83 (m, 5H), 1.77-1.11 (m, 16H), 0.88 (t, J=6.9 Hz, 3H).

$^{13}$C-NMR (Compound 8c, 151.0 MHz): 175.51, 86.05, 61.71, 43.61, 43.33, 37.17, 32.13, 30.36, 29.03, 28.01, 27.16, 25.52, 24.24, 22.66, 19.94, 14.06.

(i) Synthesis of (±)-(3-methyl-6-pentyl-1-oxa-4-azaspiro[4.4]nonan-3-yl)methanol (Compound 9)

2-Amino-2-methylpropane-1,3-diol (5.31 g, 50 mmol) and p-toluenesulfonic acid monohydrate (0.20 g) were added to a stirred solution of 2-pentylcyclopentan-1-one (8.48 g, 55 mmol) in toluene (100 mL). The mixture was heated under reflux for 22 h. After cooling to room temperature, ethyl acetate (100 mL) was added and the mixture washed with a saturated aqueous solution of $NaHCO_3$ (100 mL). The aqueous layer was re-extracted with ethyl acetate (100 mL) and the combined organic phases were washed with a saturated aqueous solution of NaCl (100 mL), dried ($Na_2SO_4$), filtered and concentrated. Column chromatography ($SiO_2$, ethyl acetate) afforded 7.07 g of the crude compound. Further column chromatography of 2.00 g ($SiO_2$, n-heptane/ethyl acetate 1:1) afforded 0.6 g (18%) of Compound 9 as a mixture of four diastereoisomers in a ratio of ca. 2.0:1.2:1:1. The compound can be used in the form of its individual separated diastereoisomers or as the non-separated mixture of isomers.

$^{1}$H-NMR (Compound 9, major isomer): 3.73-3.64 (m, 1H), 3.51-3.37 (m, 2H), 3.36-3.28 (m, 1H), 2.50-2.15 (br. m, 1H), 2.15-1.15 (m, 19H), 0.94-0.84 (m, 3H).

$^{13}$C-NMR (Compound 9, major isomer): 105.39, 73.56, 66.43, 62.55, 47.83, 39.98, 32.28, 29.62, 28.20*, 28.18*, 22.57, 22.67*, 21.33, 14.09 (*=tentative assignment).

$^{1}$H-NMR (Compound 9, second most abundant isomer): 3.73-3.64 (m, 1H), 3.55-3.37 (m, 3H), 2.50-2.15 (br. m, 1H), 2.15-1.15 (m, 19H), 0.94-0.84 (m, 3H).

$^{13}$C-NMR (Compound 9, second most abundant isomer): 105.19, 72.92, 66.69, 61.76, 48.00, 39.21, 32.22, 29.17, 28.20*, 28.01, 23.29, 22.69*, 20.83, 14.10 (*=tentative assignment).

$^{1}$H-NMR (Compound 9, minor isomers): 3.73-3.64 (m, 1H), 3.51-3.37 (m, 2H), 3.36-3.28 (m, 1H), 2.50-2.15 (br. m, 1H), 2.15-1.15 (m, 18H), 1.13-0.95 (m, 1H), 0.94-0.84 (m, 3H).

$^{13}$C-NMR (Compound 9, minor isomers): 106.34 and 105.82, 72.92 and 72.49, 66.97 and 66.67, 62.97 and 62.38, 47.18 and 47.12, 38.23 and 37.81, 32.13 and 32.11, 30.76 and 30.04, 29.00 and 28.98, 27.95 and 27.78, 23.28 and 22.95, 22.69 and 22.63, 20.74 and 20.42, 14.07 and 14.04.

(j) Synthesis of (±)-6-hexyl-1,4-diazaspiro[4.4]nonan-2-one (Compound 10)

A mixture of 2-hexylcyclopentan-1-one (5.31 g, 30 mmol), TEA (9.3 mL=9.75 g, 66 mmol, 2.2 eq.) and glycinamide hydrochloride (6.77 g, 60 mmol, 2 eq.) in methanol (50 mL) was heated under reflux for 24 h. After cooling to room temperature, the reaction mixture was filtered and the solvent was evaporated under reduced pressure. Water (50 mL) was added and the mixture extracted with ethyl acetate (2×100 mL). The combined organic phases were washed with water (50 mL) and a saturated aqueous solution of NaCl (50 mL), dried ($Na_2SO_4$), filtered and concentrated under reduced pressure. Column chromatography ($SiO_2$, n-heptane/ethyl acetate 7:3, then ethyl acetate/ethanol 1:1) afforded 3.48 g (52%) of a mixture of diastereoisomers in a ratio of ca. 1:1. The compound can be used in the form of its individual separated diastereoisomers or as the non-separated mixture of isomers.

$^{1}$H-NMR (600 MHz): 7.76 and 7.28 (br. s, 1H), 3.51 and 3.49 (d, J=16.6 and 16.2, 1 H), 3.47 and 3.41 (d, J=16.6 and 16.2, 1H), 2.05-1.60 (m, 7H), 1.54-1.08 (m, 11H), 0.88 (t, J=6.7, 3H).

$^{13}$C-NMR (150.9 MHz): 176.99 and 176.87, 86.32 and 85.33, 49.83 and 49.37, 49.03 and 48.68, 39.62 and 39.32, 31.83 and 31.80, 29.67, 29.58 and 29.42, 28.41 and 28.39, 28.31 and 28.27, 22.64 and 22.63, 20.53 and 19.81, 14.09.

(k) Synthesis of (±)-6-heptyl-1,4-diazaspiro[4.4]nonan-2-one (Compound 11)

A mixture of glycinamide hydrochloride (6.77 g, 60 mmol, 2 eq.), TEA (9.3 mL, 66 mmol, 2.2 eq.) and 2-heptylcyclopentan-1-one (5.47 g, 30 mmol) in methanol (50 mL) was heated under reflux for 24 h. After cooling to room temperature, the reaction mixture was filtered and the solvent was evaporated under reduced pressure. Water (50 mL) was added and the mixture extracted with ethyl acetate (2×100 mL). The combined organic phases were washed with water (50 mL) and a saturated aqueous solution of NaCl (50 mL), dried ($Na_2SO_4$), filtered and concentrated under reduced pressure. Column chromatography ($SiO_2$, n-heptane/ethyl acetate 7:3, then ethyl acetate and ethyl acetate/ethanol 1:1) afforded 4.35 g (61%) of a mixture of diastereoisomers in a ratio of ca. 1:1 (Compound 11). Further column chromatography ($SiO_2$, n-heptane/ethyl acetate 7:3, then ethyl acetate and ethyl acetate/ethanol 1:1) afforded several product fractions. The first fraction was filtered through cotton wool, washed with acetone, partially concentrated and placed in the freezer to give white crystals. Pipetting off the liquid and washing with a minimum of cold acetone afforded 0.11 g of white crystals of one of the diastereoisomers (Compound 11a). The second (main) fraction was re-crystallised with acetone. After filtration, the mother liquor was re-chromatographed ($SiO_2$, ethyl acetate) to give the other diastereoisomer (Compound 11b) and some mixed fractions. The compound can be used in the form of its individual separated diastereoisomers or as the non-separated mixture of isomers.

$^{1}$H-NMR (Compound 11a): 7.23 (br. s, 1H), 3.49 (d, J=16.3, 1H), 3.41 (d, J=16.3, 1 H), 1.96-1.85 (m, 3H), 1.83-1.60 (m, 4H), 1.55-1.45 (m, 1H), 1.45-1.33 (m, 2H), 1.33-1.14 (m, 10H), 0.89 (t, J=6.7, 3H).

$^{13}$C-NMR (Compound 11a): 176.95, 85.32, 49.81, 48.69, 39.33, 31.86, 29.97, 29.27, 28.44, 28.42, 28.28, 22.66, 19.81, 14.11.

$^{1}$H-NMR (Compound 11b): 7.27 (br. s, 1H), 3.51 (d, J=16.7, 1H), 3.47 (d, J=16.7, 1 H), 2.07-1.95 (m, 1H), 1.94-1.88 (m, 2H), 1.88-1.62 (m, 3H), 1.52-1.41 (m, 1H), 1.41-1.17 (m, 12H), 1.17-1.06 (m, 1H), 0.88 (t, J=6.7, 3H).

$^{13}$C-NMR (Compound 11b): 176.59, 86.18, 49.21, 48.97, 39.56, 31.84, 29.87, 29.73, 29.45, 29.29, 28.33, 22.66, 20.54, 14.11.

(l) Synthesis of methyl (±)-2-(2-oxo-6-pentyl-1,4-diazaspiro[4.4]nonan-7-yl)acetate (Compound 12)

A mixture of methyl 2-(3-oxo-2-pentylcyclopentyl)acetate (Hedione®, 6.79 g, 30 mmol), TEA (9.3 mL=9.75 g, 66 mmol) and glycinamide hydrochloride (6.77 g, 60 mmol) in methanol (50 mL) was heated under reflux for 70 h. After cooling to room temperature, the reaction mixture was concentrated under reduced pressure. Ethyl acetate (100 mL) was added and the mixture washed with an aqueous solution of NaCl (50%, 50 mL). The aqueous phase was re-extracted with ethyl acetate (100 mL), and the combined organic phases were washed with a saturated aqueous solution of NaCl (50 mL), dried ($Na_2SO_4$), filtered and concentrated under reduced pressure. Column chromatography ($SiO_2$, n-heptane/ethyl acetate 7:3, then ethyl acetate/ethanol 1:1) and bulb-to-bulb distillation of the main fraction to remove remining volatiles afforded 3.90 g (46%) of a mixture of diastereoisomers in a ratio of ca. 1:1. The compound can be used in the form of its individual separated diastereoisomers or as the non-separated mixture of isomers.

$^{1}$H-NMR (600 MHz): 7.63 and 7.44 (br. s, 1H), 3.67 (s, 3H), 3.53, 3.43 (d, J=16.2) and 3.45 (d, J=1.9) (2H), 2.58-2.52 (m, 1H), 2.37-2.21 (m, 1H), 2.20-1.84 (m, 2H), 1.83-1.71 (m, 1H), 1.63-1.18 (m, 12H), 0.88 and 0.87 (t, J=6.7, 3H).

$^{13}$C-NMR (150.9 MHz): 176.93 and 176.47, 173.20 and 173.09, 86.34 and 85.41, 53.61 and 52.67, 51.55, 49.63 and 48.82, 40.35 and 39.71, 40.24 and 39.03, 38.82 and 38.57, 32.43 and 32.27, 30.30 and 28.33, 28.23 and 28.10, 27.94 and 27.22, 22.51 and 22.48, 14.06.

Example 2

Performance of a Fabric Softener Base Comprising an Invention's Compound of Formula (I) The performance of the present invention's compounds of formula (I) was tested in a fabric softening surfactant emulsion with the following final composition:

Stepantex® VL90 A (origin: Stepan) 12.21% by weight
Calcium chloride (10% aq. solution) 0.40% by weight
Proxel® GXL (origin: Avecia) 0.04% by weight
Water 87.35% by weight (a) Dynamic Headspace Measurements The invention's compound of formula (I) (0.1 mmol) was dissolved in ethanol (0.2 mL) and added to 7.0 g of the above described fabric softener formulation. After homogenization, an aliquot of the sample (0.07 g) was diluted with demineralized cold tap water (23.0 g). Then, one cotton sheet (EMPA cotton test cloth Nr. 221, origin: Eidgenassische Materialprufanstalt), pre-washed with an unperfumed detergent powder and cut to ca. 15×15 cm sheets, ca. 5.2 g) was added and agitated manually for 3 min, left standing for 2 min, then wrung out by hand, and weighed (ca. 10.0 g) to obtain a constant quantity of residual water. A reference sample consisting of an equimolar amount of the corresponding unmodified compound of formula (VI) instead of the compound of formula (I) was prepared and analyzed the same way. The cotton sheets were line-dried for 1 or 3 days before being analyzed. For the measurements, the sheets were put into a headspace sampling cell (ca. 160 mL inner volume), which were thermostatted at 25° C. and exposed to a constant air flow of ca. 200 m/min. The air was filtered through active charcoal and aspirated through a saturated solution of NaCl (to ensure a constant humidity of the air of ca. 75%). The system was equilibrated during 15 min while adsorbing the volatiles on a waste Tenax® cartridge. Then, seven times consecutively, the volatiles were adsorbed for 15 min on a clean Tenax® cartridge and for 45 min on a waste Tenax® cartridge. The waste cartridges were discarded; the other cartridges were desorbed on a Perkin Elmer TurboMatrix ATD desorber coupled to an Agilent Technologies 7890A gas chromatograph equipped with a HP-1 capillary column (30 m, i.d. 0.32 rim, film 0.25 μm) and a FID detector. The volatiles were analyzed using a temperature gradient moving from 80° C. to 260° C. at 15° C./min. Headspace concentrations (in ng/L air) were obtained by external standard calibrations using different concentrations of the fragrance to be released in ethanol. Each calibration solution (0.2 μL) was injected onto a clean Tenax® cartridge, which was desorbed and analyzed under the same conditions. The results obtained for the release of the respective compounds of formula (VI) as compared to an equimolar amount of the corresponding unmodified compounds of formula (VI) after a total sampling time of 270 mi above dry cotton after line-drying for 1 and 3 days are summarized in Table 1. All data are average values of at least two measurements.

TABLE 1

Average headspace concentrations of compounds of formula (VI) measured after line-drying for 1 day and 3 days and sampling for 270 min on dry cotton in a fabric softener application. The factor of increase with respect to the reference is indicated in parentheses.

| Compound | Concentration of 2-(5-hexenyl) cyclopentan-1-one [ng/L] measured after line-drying for 1 day | Concentration of 2-(5-hexenyl) cyclopentan-1-one [ng/L] measured after line-drying for 3 days |
|---|---|---|
| Reference | 1.0 | 0.8 |
| Compound 1a | 7.5 (×8) | 12.4 (×16) |
| Compound 1b | 7.5 (×8) | 11.3 (×14) |
| Compound 2a | 86.7 (×87) | 15.7 (×20) |
| Compound 2b | 44.0 (×44) | 48.9 (×61) |
| Compound 3 | 84.2 (×84) | 42.1 (×53) |
| Compound | Concentration of 2-pentyl-1-cyclopentanone [ng/L] measured after line-drying for 1 day | Concentration of 2-pentyl-1-cyclopentanone [ng/L] measured after line-drying for 3 days |
| Reference | 0.7 | 0.7 |
| Compound 4 | 7.2 (×10) | 9.1 (×13) |
| Compound 5 | 5.0 (×7) | 4.0 (×6) |
| Compound 6a | 3.5 (×5) | 7.8 (×11) |
| Compound 6b | 1.9 (×3) | 2.7 (×4) |
| Compound 7 | 75.1 (×107) | 49.8 (×71) |
| Compound 7a | 53.1 (×76) | 58.5 (×84) |
| Compound 7b | 78.6 (×112) | 33.2 (×46) |
| Compound 7c | 57.8 (×83) | 28.5 (×41) |
| Compound 8 | 2.5 (×4) | 1.3 (×2) |
| Compound 9 | 32.8 (×47) | 7.5 (×11) |

TABLE 1-continued

Average headspace concentrations of compounds of formula (VI) measured after line-drying for 1 day and 3 days and sampling for 270 min on dry cotton in a fabric softener application. The factor of increase with respect to the reference is indicated in parentheses.

| Compound | Concentration of 2-hexyl-1-cyclopentanone [ng/L] measured after line-drying for 1 day | Concentration of 2-hexyl-1-cyclopentanone [ng/L] measured after line-drying for 3 days |
|---|---|---|
| Reference | 1.1 | 1.3 |
| Compound 10 | 13.6 (×12) | 12.3 (×9) |

The compounds according to formula (I) released higher amounts of compounds of formula (VI) into the headspace above dry cotton than the reference sample consisting of an equimolar amount of the corresponding unmodified compound of formula (VI). Compounds of formula (I) according to the present invention are thus capable to increase the long-lastingness for the perception of perfumery ingredients derived from cyclopentanone.

(b) Sensory Panel Evaluations

The performance of the present invention's compounds of formula (I) was tested in a fabric softening surfactant emulsion with the following composition:

Methyl bis[ethyl(tallowate)]-2-hydroxyethyl ammonium methyl sulfate[1)] 8.88

Calcium chloride sol 10% 0.36

1,2-benzisothiazolin-3-one[2)] 0.04

Water 90.72

1) Stepantex® VL 90A-Stepan

2) Proxel® GXL—Arch

The softener was prepared by weighting methyl bis[ethyl (tallowate)]-2-hydroxyethyl ammonium methyl sulfate which was heated at 65° C. Then, water and 1,2-benzisothiazolin-3-one were placed in the reactor and were heated at 65° C. under stirring. To the above mixture was added methyl bis[ethyl (tallowate)]-2-hydroxyethyl ammonium methyl sulfate. The mixture was stirred 15 minutes and $CaCl_2$ was added. Then 0.1 g of Compound 7 or 0.0616 g 2-pentylcyclopentanone was added. The mixture was stirred 15 minutes and was cooled down to room temperature under stirring (viscosity measure: result 35+/−5 mPas. (shear rate 106 sec−1)).

Cotton terry towels (36 pieces, 18 cm*18 cm, about 30 g each) were washed with 55 g of unperfumed detergent in a European washing machine (Miele Novotronic W300-33CH) at 40° C. using the short cycle program. The wash was followed by a rinse at 900 rpm with 23 g of above concentrated fabric-softener. The terry towels were then line dried for 24 hours before being evaluated by a panel of 20 trained panelists. The panelists were asked to rate the odor intensity of the towels after gentle rubbing of the fabrics by hand on a scale from 1 to 7, 1 corresponding to odorless and 7 corresponding to a very strong odor. The results obtained are summarized in Table 2.

TABLE 2

Panel evaluation in a fabric softener application.

| | Line Drying | | |
|---|---|---|---|
| Overall Perfume Intensity | 1 day | 3 days | 7 days |
| Softener + 0.1% of Compound 7 | 2.19 | 3.29 | 3.28 |
| Softener + 0.0616% of 2-pentylcyclopentanone | 2.23 | 2.50 | 2.04 |

Olfactive performance on dry fabrics due to the presence of properfume Compound 7 had relatively close performance to the 2-pentylcyclopentanone control at Day 1 and was perceived significantly more intense than the 2-pentylcyclopentanone control at Day 3 and Day 7. Based on the results, the pro-perfume Compound 7 at 0.1% performed significantly better than 2-pentylcyclopentanone control at 0.0616%, at least from dry 3 days up to dry 7 days.

Example 3

Performance of an all-purpose hard surface cleaner formulation comprising an invention's compound of formula (I)

The release of compounds of formula (VI) from the present invention's compounds of formula (I) was tested in an all-purpose surface cleaner (APC). An APC formulation with the following final composition has been prepared:

Neodol® 91-8 (origin: Shell Chemicals) 5.0% by weight
Marlon® A 375 (origin: Hüls AG) 4.0% by weight
Sodium cumolsulphonate 2.0% by weight
Kathon® CG (origin: Rohm and Haas) 0.2% by weight
Deionized water 88.8% by weight In a flask, one of the invention's compounds of formula (I) (0.0369 mmol) was dissolved in ethanol (100 µL). Then the APC formulation (3.0 mL) was added and the sample shaken gently. An aliquot of these samples (1 mL) was pipetted off and diluted with demineralized tap water (9 mL). A film of this solution (0.75 mL) was pipetted onto a porous ceramic plate (ca. 5×10 cm) and left standing at room temperature. Similarly, a reference sample consisting of an equimolar amount of the corresponding unmodified compound of formula (VI) (0.0369 mmol) instead of one of the invention's compounds of formula (I) in ethanol (100 µL) was prepared and processed the same way.

After one day, each of the ceramic plates was placed inside a headspace sampling cell (ca. 625 mL) and exposed to a constant air flow of ca. 200 mL/min. The air was filtered through active charcoal and aspirated through a saturated aqueous solution of NaCl (to ensure a constant humidity of the air of ca. 75%). The headspace system was equilibrated for 15 min by adsorbing the volatiles onto a waste Tenax® cartridge. Then the volatiles were alternately adsorbed for 10 min onto a clean Tenax® cartridge and for 20 min onto a waste Tenax® cartridge (6×). The waste cartridges were discarded; the clean cartridges were desorbed and analyzed as described in Example 2. All measurements were performed at least twice. The average headspace concentrations of compounds of formula (VI) released from the compounds of formula (I) as prepared in Example 1 or from the reference sample after 55 min of sampling above the porous ceramic plates are listed in Table 3. Table 3 also indicates the factors of increase of compounds of formula (VI) released from the invention's compounds of formula (I) with respect to the reference sample.

TABLE 3

Average headspace concentrations of compounds of formula (VI) measured after drying for 1 day and sampling 55 min of sampling above ceramic plates in an APC application. The factor of increase with respect to the reference is indicated in parentheses.

| Compound | Concentration of 2-(5-hexenyl)cyclopentan-1-one [ng/L] after drying for 1 day |
|---|---|
| Reference | 15.5 |
| Compound 2 | 70.7 (×5) |
| | Concentration of 2-pentyl-1-cyclopentanone [ng/L] after drying for 1 day |
| Reference | 5.5 |
| Compound 9 | 186.4 (×34) |
| | Concentration of 2-heptyl-1-cyclopentanone [ng/L] after drying for 1 day |
| Reference | 17.3 |
| Compound 11 | 35.3 (×2) |

After 1 day, the invention's compounds of formula (I) as prepared in Example 1 release more compound of formula (VI) into the headspace than the reference sample. The invention's compounds of formula (I) are thus able to provide a long-lasting and substantive release of compounds of formula (VI) to a hard surface from an APC application.

Example 4

Performance of a Hair Conditioning Formulation Comprising an Invention's Compound of Formula (I)

The generation of compounds of formula (VI) from the present invention's compounds of formula (I) was tested in a hair conditioning application. A hair conditioning formulation with the following final composition has been prepared:

Dehyquart® C 4046 (origin: BASF) 5.00% by weight
Glycerin (85%) (origin: Brenntag) 2.00% by weight
Paraffinum Perliquidum (origin: Acros) 2.00% by weight
Genamin® CTAC (origin: Clariant) 1.00% by weight
Xiameter MEM-949 Cationic Emulsion (origin: Xiameter) 1.00% by weight
Jaguar® C14 S (origin: Lubrizol) 0.30% by weight
Kathon® CG (origin: Rohm and Haas) 0.08% by weight
EDTA B Powder (origin: BASF) 0.05% by weight
Deionized water 88.57% by weight A solution of one of the present invention's compounds of formula (I) in ethanol was prepared by weighing precisely 0.3 mmol of the compound into a volumetric flask (5 mL) and filling up with ethanol. Similarly, a reference solution containing an equimolar amount of the compound of formula (VI) to be released was prepared.

The hair conditioner formulation described above (920 mg) was weighed in a sample tube (3 mL), then the ethanol solution (100 μL) containing one of the invention's compounds of formula (I) or (VI, reference) were added. The tube was closed, shaken (50×) and centrifuged with a manual centrifuge (at ca. 3500 rpm) during 30 s.

A Caucasian hair swatch (origin: Kerling International Haarfabrik GmbH, ca. 10 cm long, about 0.5 g) was rinsed and rubbed under tap water at 37° C. with a flow of ca. 2 L/min for 30 s, and the excess of water was squeezed out with the fingertips. An unperfumed shampoo formulation (0.1 g) was spread onto the hair swatch, which was washed for 30 s. Then the shampoo was rinsed off with tap water at 37° C. for 30 s, and the excess of water was squeezed out with the fingertips. Then the hair conditioning formulation (0.1 g), containing either one of the invention's compounds according to formula (I) or the reference compound of formula (VI), was spread onto the hair swatch. The hair swatch was gently rubbed between the fingertips for 1 min, combed once and line-dried.

After 6 h, the hair swatch was combed (10×) and fixed with adhesive tape inside a thermostatted (25° C.) headspace sampling cell with an inner volume of ca.165 mL. A constant flow of air (200 mL/min) was pumped across the sample. The incoming air was filtered through active charcoal, and through a saturated aqueous solution of NaCl. The system was equilibrated for 10 min by absorbing the volatiles onto a waste Tenax® cartridge. Then the volatiles were adsorbed for 10 min onto a first clean Tenax® cartridge and for another 10 min onto a second clean Tenax® cartridge. Then the pump was stopped. The hair swatch was left inside the headspace sampling cell without connecting a cartridge. After 24 h a waste Tenax® cartridge was connected, the pump was switched on and the system was equilibrated for 10 min. Then the volatiles were consecutively adsorbed for 10 min onto two clean Tenax® cartridges. The waste cartridges were discarded; the clean cartridges were desorbed and analyzed as described in Example 2. All measurements were performed at least twice.

The average headspace concentrations of 2-pentyl-1-cyclopentanone (compound of formula (VI)) released from Compound 9 (compound of formula (I), as prepared in Example 1) or from the reference sample (desorbed from the first cartridge) after 6 h and after 24 h are listed in Table 4. Table 4 also indicates the factors of increase of the fragrance released from the invention's compounds of formula (I) with respect to the reference sample.

TABLE 4

Average headspace concentrations of 2-pentyl-1-cyclopentanone measured after drying for 6 and 24 h on hair in a hair conditioning application. The factor of increase with respect to the reference is indicated in parentheses.

| | Concentration of 2-pentyl-1-cyclopentanone [ng/L] measured after drying for 6 h | Concentration of 2-pentyl-1-cyclopentanone [ng/L] measured after drying for 24 h |
|---|---|---|
| Reference | 1.9 | 4.2 |
| Compound 9 | 40.3 (×21) | 152.7 (×36) |

The invention's compounds of formula (I) as prepared in Example 1 release higher amounts of fragrance into the headspace than the reference sample, especially after longer periods of time (24 h). The invention's compounds of formula (I) are thus able to provide a long-lasting and substantive perfume odor to hair from a hair conditioning application.

Example 5

Preparation of a Perfume Oil

A non-limiting example of a typical perfume oil is prepared by admixing the following perfuming co-ingredients:

| Ingredients | weight-% |
|---|---|
| Ethyl 2-methylbutanoate | 0.16 |
| Hexyl acetate | 0.37 |
| Limonene | 1.67 |
| 2,6-Dimethyl-7-octen-2-ol | 0.94 |
| 2-Phenylethanol | 2.15 |
| Linalool | 0.73 |
| (2RS,4SR/4RS)-4-Methyl-2-(2-methyl-1-propen-1-yl) tetrahydro-2H-pyran | 0.30 |
| Ethyl 2-methyl-1,3-dioxolane-2-acetate | 0.32 |
| Benzyl acetate | 2.46 |
| Allyl heptanoate | 0.38 |
| alpha-Terpineol | 0.88 |
| 3,7-Dimethyl-6-octen-1-ol | 0.55 |
| 4-Methoxybenzaldehyde | 1.00 |
| (E)-4-Methyl-3-decen-5-ol | 0.37 |
| [cis/trans-4-(2-Propanyl)cyclohexyl]methanol | 0.47 |
| 1-Methoxy-4-[(1E)-1-propen-1-yl]benzene | 0.15 |
| (1RS,2RS/2SR)-2-(2-Methyl-2-propanyl)cyclohexyl acetate | 1.95 |
| 1,1-Dimethyl-2-phenylethyl acetate | 0.95 |
| Tricyclo[5.2.1.$0^{2,6}$]dec-3/4-en-8-yl acetate | 3.34 |
| Allyl 3-cyclohexylpropanoate | 0.26 |
| 3-(4-Isopropylphenyl)-2-methylpropanal | 8.18 |
| (3E)-3-Methyl-4-(2,6,6-trimethyl-2-cyclohexen-1-yl)-3-buten-2-one and (1E)-1-(2,6,6-trimethyl-2-cyclohexen-1-yl)-1-penten-3-one | 1.13 |
| 2-Phenoxyethyl 2-methylpropanoate | 5.38 |
| Tricyclo[5.2.1.0(2,6)]dec-3/4-en-8-yl propanoate | 2.32 |
| 5-Heptyldihydro-2(3H)-furanone | 2.30 |
| 2/3-Methylbutyl salicylate | 1.42 |
| (3Z)-3-Hexen-1-yl salicylate | 0.31 |
| 1-(2,3,8,8-Tetramethyl-1,3,4,5,6,7-hexahydronaphthalen-2-yl) ethanone | 16.03 |
| Hexyl 2-hydroxybenzoate | 5.04 |
| (2E)-2-Benzylideneoctanal | 21.22 |
| (-)-(3aR,5aS,9aS,9bR)-3a,6,6,9a-Tetramethyldodecahydronaphtho[2,1-b]furan | 0.27 |
| 1-Oxa-12/13-cyclohexadecen-2-one | 4.78 |
| Oxacyclohexadecan-2-one | 3.82 |
| Benzyl 2-hydroxybenzoate | 3.01 |
| Dipropylene glycol | 5.39 |
| Total: | 100 |

Example 6

Preparation of Transparent Isotropic Shampoo Formulations Comprising an Invention's Compound of Formula (I)

A typical unperfumed transparent isotropic shampoo formulation is listed in Table 5. The unperfumed shampoo formulation is prepared by dispersing Polyquaternium-10 in water. The remaining ingredients of Phase A are mixed separately by addition of one after the other while mixing well after each adjunction. This pre-mix is added to the Polyquaternium-10 dispersion and mixed for another 5 min. Then, the premixed Phase B and the premixed Phase C are added (Monomuls® 90L-12 is heated to melt in Texapon® NSO IS) while agitating. Phase D and Phase E are added while agitating. The pH is adjusted with a citric acid solution to 5.5-6.0.

TABLE 5

Composition of a typical unperfumed transparent isotropic shampoo formulation.

| Phase | Ingredients | Amount [wt %] |
|---|---|---|
| A | Deionized water | 44.4 |
| | Polyquaternium-10 [(1)] | 0.3 |
| | Glycerin 85% [(2)] | 1.0 |
| | DMDM Hydantoin [(3)] | 0.2 |
| B | Sodium laureth sulfate [(4)] | 28.0 |
| | Cocamidopropyl betaine [(5)] | 3.2 |
| | Disodium cocoamphodiacetate [(6)] | 4.0 |
| | Ethoxy (20) stearyl alcohol [(7)] | 1.0 |
| C | Sodium laureth sulfate [(4)] | 3.0 |
| | Glyceryl laureate [(8)] | 0.2 |
| D | Deionized water | 1.0 |
| | Sodium methylparaben [(9)] | 0.1 |
| E | Sodium chloride (10% aqueous solution) | 15.0 |
| | Citric acid (10% aqueous solution to pH 5.5-6.0) | q.s. |

(1) Ucare ® Polymer JR-400; origin: Noveon
(2) Origin: Brenntag Schweizerhall AG
(3) Glydant ®; origin: Lonza
(4) Texapon ® NSO IS; origin: Cognis
(5) Tego ® Betain F 50; origin: Evonik
(6) Amphotensid GB 2009; origin: Zschimmer & Schwarz
(7) Brij ® S20; origin: Croda
(8) Monomuls ® 90 L-12; origin: Gruenau GmbH
(9) Nipagin Monosodium; origin: NIPA The perfumed shampoo formulation is then obtained by adding, under gentle shaking, a perfume oil (as e.g. described in Example 5, 0.1 to 0.8% by weight relative to the total weight of the unperfumed shampoo formulation) and at least one of the compounds of formula (I) (0.05 to 0.50% by weight relative to the total weight of the unperfumed shampoo formulation) into the unperfumed shampoo formulation listed in Table 5.

Example 7

Preparation of pearly shampoo formulations comprising an invention's compound of formula (I)

A typical unperfumed pearly shampoo formulation is listed in Table 6. The unperfumed shampoo formulation is prepared by dispersing Tetrasodium EDTA, Guar hydroxypropyltrimonium chloride and Polyquaternium-10 in water. NaOH (10% aqueous solution, Phase B) is added once Phase A is homogeneous. Then, the premixed Phase C is added, and the mixture heated to 75° C. Phase D ingredients are added and mixed until the mixture is homogeneous. The mixture is cooled. At 45° C., Phase E ingredients are added while mixing. The final viscosity is adjusted with NaCl (25% aqueous solution) and a pH of 5.5-6.0 is adjusted with NaOH (10% aqueous solution).

TABLE 6

Composition of a typical pearly shampoo formulation.

| Phase | Ingredients | Amount [wt %] |
|---|---|---|
| A | Deionized water | 45.97 |
| | Tetrasodium EDTA [(1)] | 0.05 |
| | Guar hydroxypropyl-trimonium chloride [(2)] | 0.05 |
| | Polyquaternium-10 [(3)] | 0.075 |
| B | NaOH (10% aqueous solution) | 0.30 |
| C | Ammonium lauryl sulfate [(4)] | 34.00 |
| | Ammonium laureth sulfate [(5)] | 9.25 |
| | Cocamidopropyl betaine [(6)] | 2.00 |

TABLE 6-continued

Composition of a typical pearly shampoo formulation.

| Phase | Ingredients | Amount [wt %] |
|---|---|---|
| | Dimethicone (&) $C_{12-13}$ pareth-4 (&) $C_{12-13}$ pareth-23 (&) salicylic acid (7) | 2.50 |
| D | Cetyl alcohol (8) | 1.20 |
| | Cocamide MEA (9) | 1.50 |
| | Glycol distearate (10) | 2.00 |
| E | Methylchloroisothiazolinone & methylisothiazolinone (11) | 0.10 |
| | D-Panthenol 75% (12) | 0.10 |
| | Deionized water | 0.30 |
| F | Sodium chloride (25% aqueous solution) | 0.60 |

(1) EDETA ® B Powder; origin: BASF
(2) Jaguar ® C14 S; origin: Rhodia
(3) Ucare® Polymer JR-400; origin: Noveon
(4) Sulfetal ® LA B-E; origin: Zschimmer & Schwarz
(5) Zetesol ® LA; origin: Zschimmer & Schwarz
(6) Tego ® Betain F 50; origin: Evonik
(7) Xiameter ® MEM-1691; origin: Dow Corning
(8) Lanette ® 16; origin: BASF
(9) Comperlan ® 100; origin: Cognis
(10) Cutina ® AGS; origin: Cognis
(11) Kathon ® CG; origin: Rohm & Haas
(12) D-Panthenol; origin: Roche A perfumed pearly shampoo formulation is then obtained by adding, under gentle shaking, a perfume oil (as e.g. described in Example 5, 0.1 to 0.8% by weight relative to the total weight of the unperfumed shampoo formulation) and at least one of the compounds of formula (I) (0.05 to 0.50% by weight relative to the total weight of the unperfumed shampoo formulation) into the unperfumed pearly shampoo formulation listed in Table 6.

Example 8

Preparation of Rinse-Off Hair Conditioner Formulations Comprising an Invention's Compound of Formula (I)

A typical unperfumed rinse-off hair conditioner formulation is listed in Table 7. The unperfumed rinse-off hair conditioner formulation is prepared by mixing the ingredients of Phase A until an uniform mixture was obtained. Tylose® is allowed to completely dissolve. Then the mixture is heated to 70-75° C. The ingredients of Phase B are combined and melted at 70-75° C. Then the ingredients of Phase B are added to Phase A with good agitation, and the mixing is continued until that the mixture has a temperature of 60° C. Then, the ingredients of Phase C are added while agitating and keeping mixing until the mixture cooled to 40° C. The pH is adjusted with a citric acid solution to 3.5-4.0.

TABLE 7

Composition of a typical rinse-off hair conditioner formulation.

| Phase | Ingredients | Amount [wt %] |
|---|---|---|
| A | Deionized water | 81.8 |
| | Behentrimonium chloride (1) | 2.5 |
| | Hydroxyethylcellulose (2) | 1.5 |
| B | Cetearyl alcohol (3) | 4.0 |
| | Glyceryl stearate (and) PEG-100 stearate (4) | 2.0 |
| | Behentrimonium metho-sulfate (and) cetyl alcohol (and) butylene glycol (5) | 4.0 |
| | Ethoxy (20) stearyl alcohol (6) | 1.0 |
| C | Amodimethicone (and) Trideceth-12 (and) Cetrimonium chloride (7) | 3.0 |
| | Chlorhexidine digluconate (20% aqueous solution) (8) | 0.2 |
| D | Citric acid (10% aqueous solution tol pH 3.5-4.0) | q.s. |

(1) Genamin ® KDMP; origin: Clariant
(2) Tylose ® H10 Y G4; origin: Shin Etsu
(3) Lanette ® O; origin: BASF
(4) Arlacel ® 165; origin: Croda
(5) Incroquat ® Behenyl TMS-50-PA-(MH); origin: Croda
(6) Brij ® S20; origin: Croda
(7) Xiameter ® MEM-949; origin: Dow Corning
(8) Origin: Alfa Aesar A perfumed rinse-off hair conditioner formulation is then obtained by adding, under gentle shaking, a perfume oil (as e.g. described in Example 5, 0.2 to 1.0% by weight relative to the total weight of the unperfumed conditioner formulation) and at least one of the compounds of formula (I) (0.05 to 0.5% by weight relative to the total weight of the unperfumed conditioner formulation) into the unperfumed rinse-off hair conditioner formulation listed in Table 7.

Example 9

Preparation of Structured Shower Gel Formulations Comprising an Invention's Compound of Formula (I)

A typical unperfumed structured shower gel formulation is listed in Table 8. A perfumed structured shower gel is prepared by adding, under gentle shaking, a perfume oil (as e.g. described in Example 5, 0.1 to 1.5% by weight relative to the total weight of the structured shower gel) and at least one of the invention's compounds of formula (I) (0.05 to 0.50% by weight relative to the total weight of the structured shower gel) into the unperfumed structured shower gel formulation of Table 8.

TABLE 8

Composition of a typical unperfumed structured shower gel formulation.

| Ingredients | Amount [wt %] |
|---|---|
| Deionized water | 49.35 |
| Tetrasodium EDTA (1) | 0.05 |
| Acrylates co-polymer (2) | 6.00 |
| Sodium $C_{12-15}$ pareth sulfate (3) | 35.00 |
| Sodium hydroxide (20% aqueous solution) | 1.00 |
| Cocamidopropyl betaine (4) | 8.00 |
| Methylchloroisothiazolinone and methylisothiazolinone (5) | 0.10 |
| Citric acid (40% aqueous solution) | 0.50 |

(1) EDETA B powder; origin: BASF
(2) Carbopol Aqua SF-1 polymer; origin: Noveon
(3) Zetesol AO 328 U; origin: Zschimmer & Schwarz
(4) Tego Betain F 50; origin: Goldschmidt
(5) Kathon ® CG; origin: Rohm & Haas

Example 10

Preparation of Transparent Shower Gel Formulations Comprising an Invention's Compound of Formula (I)

A typical unperfumed transparent shower gel formulation is listed in Table 9. A perfumed transparent shower gel is prepared by adding, under gentle shaking, a perfume oil (as e.g. described in Example 5, 0.5 to 1.5% by weight relative to the total weight of the transparent shower gel) and at least one of the invention's compounds of formula (I) (0.05 to 0.50% by weight relative to the total weight of the transparent shower gel) into the unperfumed transparent shower gel formulation of Table 9.

TABLE 9

Composition of a typical unperfumed transparent shower gel formulation

| Ingredients | Amount [wt %] |
|---|---|
| Deionized water | 52.40 |
| Tetrasodium EDTA [(1)] | 0.10 |
| Sodium benzoate | 0.50 |
| Propylene glycol | 2.00 |
| Sodium $C_{12-15}$ pareth sulfate [(2)] | 35.00 |
| Cocamidopropyl betaine [(3)] | 8.00 |
| Polyquaternium-7 [(4)] | 0.20 |
| Citric acid (40% aqueous solution) | 1.00 |
| Sodium chloride | 0.80 |

(1) EDETA B powder; origin: BASF
(2) Zetesol AO 328 U; origin: Zschimmer & Schwarz
(3) Tego Betain F 50; origin: Goldschmidt
(4) Merquat ® 550; origin: Lubrizol Example 11

Preparation of Milky Shower Gel Formulations Comprising an Invention's Compound of Formula (I)

A typical unperfumed milky shower gel formulation is listed in Table 10. A perfumed milky shower gel is prepared by adding, under gentle shaking, a perfume oil (as e.g. described in Example 5, 0.1 to 1.5% by weight relative to the total weight of the milky shower gel) and at least one of the invention's compounds of formula (I) (0.05 to 0.50% by weight relative to the total weight of the milky shower gel) into the unperfumed milky shower gel formulation of Table 10.

TABLE 10

Composition of a typical unperfumed milky shower gel formulation.

| Ingredients | Amount [wt %] |
|---|---|
| Deionized water | 50.95 |
| Tetrasodium EDTA [(1)] | 0.05 |
| Sodium benzoate | 0.50 |
| Glycerin (86% aqueous solution) | 3.50 |
| Sodium laureth sulfate [(2)] | 27.00 |
| Polyquaternium-7 [(3)] | 1.00 |
| Coco-betaine [(4)] | 6.00 |
| PEG-120 Methyl glucose trioleate [(5)] | 1.00 |
| Citric acid (40% aqueous solution) | 1.00 |
| Glycol distearate & laureth-4 & cocamidopropyl betaine [(6)] | 3.00 |
| Sodium chloride (20% aqueous solution) | 5.00 |
| PEG-40 hydrogenated castor oil [(7)] | 1.00 |

(1) EDETA ® B powder; origin: BASF
(2) Texapon ® NSO IS; origin: Cognis
(3) Merquat ® 550; origin: Lubrizol
(4) Dehyton ® AB-30; origin: Cognis
(5) Glucamate ® LT; origin: Lubrizol
(6) Euperlan ® PK 3000 AM; origin: Cognis
(7) Cremophor ® RH 40; origin: BASF Example 12

Preparation of Anhydrous Antiperspirant Spray Formulations Comprising an Invention's Compound of Formula (I)

A typical unperfumed anhydrous antiperspirant spray formulation is listed in Table 11. The anhydrous antiperspirant spray formulation is prepared by using a high speed stirrer. Silica and Quaternium-18-hectorite are added to the mixture of isopropyl myristate and cyclomethicone. Once completely swollen, aluminium chlorohydrate is added portion-wise under stirring until the mixture becomes homogeneous and without lumps.

TABLE 11

Composition of a typical unperfumed anhydrous antiperspirant spray.

| Ingredients | Amount [wt %] |
|---|---|
| Cyclomethicone [(1)] | 53.51 |
| Isopropyl myristate | 9.04 |
| Silica [(2)] | 1.03 |
| Quaternium-18-hectorite [(3)] | 3.36 |
| Aluminium chlorohydrate [(4)] | 33.06 |

(1) Dow Corning ® 345 Fluid; origin: Dow Corning
(2) Aerosil ® 200 ; origin: Evonik
(3) Bentone ® 38; origin: Elementis Specialities
(4) Micro Dry Ultrafine; origin: Reheis The perfumed formulation is then obtained by adding a perfume oil (as e.g. described in Example 5, 0.85% by weight relative to the total weight of the antiperspirant spray formulation) and at least one of the invention's compounds of formula (I) (0.15% by weight relative to the total weight of the antiperspirant spray formulation) into the unperfumed antiperspirant spray formulation of Table 11.

Example 13

Preparation of Deodorant Spray Emulsion Formulations Comprising an Invention's Compound of Formula (I)

A typical deodorant spray emulsion formulation is prepared by mixing and dissolving all the ingredients according to the sequence of Table 12. Then a perfume oil (as e.g. described in Example 5, 1.35% by weight relative to the total weight of the deodorant spray formulation) and at least one of the invention's compounds of formula (I) (0.10 to 0.20% by weight relative to the total weight of the deodorant spray formulation) are added under gentle shaking. Then aerosol cans are filled, and the propellant is crimped and added. Aerosol filling: 40% active solution 60% propane/butane (2.5 bar).

TABLE 12

Composition of a typical unperfumed deodorant spray formulation.

| Ingredients | Amount [wt %] |
|---|---|
| Ethanol (95%) | 90.65 |
| Triclosan [(1)] | 0.26 |
| Isopropyl myristate | 9.09 |

(1) Irgasan ® DP 300; origin: BASF

Example 14

Preparation of deodorant stick formulations comprising an invention's compound of formula (I)

A typical unperfumed deodorant stick formulation is listed in Table 13. The deodorant stick formulation is obtained by weighing all the components of Part A and heating to 70-75° C. Ceteareth-25 is added once the other Part A ingredients are mixed and heated. Once the Ceteareth-25 is dissolved, stearic acid is added. Part B is prepared by dissolving Triclosan in 1,2-propylene glycol. Evaporated water is compensated. Then, slowly, under mixing, Part B is poured into Part A.

TABLE 13

Composition of a typical unperfumed deodorant stick formulation.

| Phase | Ingredients | Amount [wt %] |
|---|---|---|
| A | Stearic acid | 5.05 |
| | 1,2-Propylene glycol | 41.87 |
| | Sodium hydroxide (20% aqueous solution) | 4.24 |
| | Water | 30.30 |
| | Tetrasodium EDTA (1) | 0.10 |
| | Ceteareth-25 (2) | 1.52 |
| | PPG-3 Myristyl ether (3) | 1.52 |
| B | 1,2-Propylene glycol | 15.14 |
| | Triclosan (4) | 0.25 |

(1) Edeta ® B Power; origin: BASF
(2) Cremophor ® A25; origin: BASF
(3) Tegosoft ® APM; origin: Evonik
(4) Irgasan ® DP 300; origin: BASF The perfumed deodorant stick formulation is then obtained by adding perfume oil (as e.g. described in Example 5, 0.85% by weight relative to the total weight of the deodorant stick formulation) and at least one of the invention's compounds of formula (I) (0.10 to 0.20% by weight relative to the total weight of the deodorant stick formulation) under gentle shaking. To stock, a plastic bag is put into the bucket to be sealed after cooling. Moulds were filled at about 70° C.

Example 15

Preparation of Deodorant Roll-on Formulations Comprising an Invention's Compound of Formula (I)

A typical unperfumed deodorant roll-on formulation is listed in Table 14. Part A is prepared by sprinkling little-by-little the hydroxyethylcellulose into the water, whilst rapidly stirring with a turbine until the hydroxyethylcellulose is entirely swollen giving a limpid gel. Part B is slowly poured into Part A, whilst continuing stirring until the entire mixture is homogeneous. Then Part C is added.

TABLE 14

Composition of a typical unperfumed deodorant roll-on formulation.

| Phase | Ingredients | Amount [wt %] |
|---|---|---|
| A | Water | 50.51 |
| | Hydroxyethylcellulose (1) | 0.71 |
| B | Ethanol (95%) | 40.40 |
| | 1,2-Propylene glycol | 5.05 |
| | Triclosan (2) | 0.30 |
| C | PEG-40 hydrogenated castor oil (3) | 3.03 |

(1) Natrosol ® 250 H; origin: Ashland
(2) Irgasan ® DP 300; origin: BASF
(3) Cremophor ® RH 40; origin: BASF The perfumed deodorant roll-on formulation is then obtained by adding perfume oil (as e.g. described in Example 5, 0.85% by weight relative to the total weight of the deodorant stick formulation) and at least one of the invention's compounds of formula (I) (0.10-0.20% by weight relative to the total weight of the deodorant stick formulation) under gentle shaking.

Example 16

Preparation of Day Cream Base O/W Emulsions Comprising an Invention's Compound of Formula (I)

A typical day cream base O/W emulsion formulation comprising an invention's compound of formula (I) is listed in Table 15. Phases A and B are heated separately to 70-75° C., then Phase A is added to Phase B and vacuum is applied. The mixture is stirred and cooled to 55° C. for 15 min. After cooling to room temperature, phenoxyethanol (and) piroctone olamine (Part C) are added when a temperature of 45° C. is reached. The mixture is stirred for 5 min before sodium carbomer (Part D), a perfume oil (as e.g. described in Example 5) and at least one of the invention's compounds of formula (I) (Part E) are added. The mixture is stirred for 3 min, then the stirring was stopped for 15 min. When the temperature of the mixture reaches 30° C., the stirring is resumed for another 15 min until the cream becomes homogeneous, glossy and without lumps. If necessary the pH is adjusted to 6.70-7.20 with Glydant®, Phenoni®p or Nipaguard® P05 or to 6.30-7.00 with Nikkoguard®.

TABLE 15

Composition of a typical day cream base O/W emulsion.

| Phase | Ingredients | Amount [wt %] |
|---|---|---|
| A | Steareth-2 (and) PEG-8 Distearate(1) | 5.0 |
| | Cetyl alcohol | 0.5 |
| | Ceteth-20 (and) glyceryl stearate (and) PEG-6 stearate (and) Steareth-20 (2) | 4.0 |
| | Squalan (3) | 1.0 |
| | Paraffin oil (4) | 2.0 |
| | Petrolatum (5) | 5.5 |
| B | Deionized water | 75.9 |
| | Propylene glycol | 5.0 |
| C | Phenoxyethanol (and) Piroctone olamine (6) | 0.6 |
| D | Sodium carbomer (7) | 0.2 |
| E | Perfume oil (as in Example 5) | 0.15 |
| | Compound of formula (I) | 0.15 |

(1) Arlacel ® 985; origin: Croda
(2) Tefose ® 2561; origin: Gattefosse
(3) Biolip P 90; origin: Gattefosse
(4) Mineral oil 30-40 CPS
(5) Petroleum jelly
(6) Nipaguard ® PO 5; origin: Clariant
(7) PNC 400

Example 17

Preparation of Liquid Detergent Formulations Comprising an Invention's Compound of Formula (I)

A typical liquid detergent formulation is prepared by mixing the ingredients listed in Table 16. Then a perfume oil (as e.g. described in Example 5, 0.3 to 0.8% by weight relative to the total weight of the liquid detergent) and at least one of the invention's compounds of formula (I) (0.05 to 1.0% by weight relative to the total weight of the liquid detergent) are added under gentle shaking into the unperfumed liquid detergent formulation of Table 16.

TABLE 16

| Composition of a typical unperfumed liquid detergent formulation. | |
|---|---|
| Ingredients | Amount [wt %] |
| Sodium $C_{14-17}$ alkyl sec. sulfonate (1) | 7.0 |
| Fatty acids, $C_{12-18}$ and $C_{18}$-unsaturated (2) | 7.5 |
| $C_{12/14}$ fatty alcohol polyglycol ether with 7 mol EO (3) | 17.0 |
| Triethanolamine | 7.5 |
| Propylene glycol | 11.0 |
| Citric acid | 6.5 |
| Potassium hydroxyde | 9.5 |
| Properase ® L (4) | 0.2 |
| Puradax ® EG L (4) | 0.2 |
| Purastar ® ST L (4) | 0.2 |
| Acrylates/Steareth-20 methacrylate structuring crosspolymer (5) | 6.0 |
| Deionized water | 27.4 |

(1) Hostapur ® SAS 60; origin: Clariant
(2) Edenor ® K 12-18; origin: Cognis
(3) Genapol ® LA 070; origin: Clariant
(4) Origin: Genencor International
(5) Aculyn ® 88; origin: Dow Chemicals

Example 18

Preparation of Hand Dishwash Formulations Comprising an Invention's Compound of Formula (I)

A typical unperfumed hand dishwash formulation is listed in Table 17. The unperfumed hand dishwash is prepared by mixing water with sodium hydroxide and diethanolamide. Then the linear alkylbenzene sulfonic acid is added. After neutralizing, the remaining ingredients are added and the pH is adjusted to 7-8 if necessary.

TABLE 17

| Composition of a typical unperfumed hand dishwash formulation. | |
|---|---|
| Ingredients | Amount [wt %] |
| Linear alkylbenzene sulfonic acid (1) | 20.0 |
| Diethanolamide (2) | 3.5 |
| Sodium hydroxide (50%) (3) | 3.4 |
| Secondary alcohol ethoxolate (4) | 2.5 |
| Sodium xylene sulfonate | 6.3 |
| Deionized water | 64.3 |

(1) Biosoft ® S-118; origin: Stepan
(2) Ninol ® 40-CO; origin: Stepan
(3) Stepanate ® SXS; origin: Stepan
(4) Tergitol ® 15-S-9; origin: Dow Chemicals The perfumed hand dishwash formulation is then obtained by adding perfume oil (as e.g. described in Example 5, 0.85% by weight relative to the total weight of the hand dishwash formulation) and at least one of the invention's compounds of formula (I) (0.10 to 0.20% by weight relative to the total weight of the dishwash formulation) under gentle shaking into the unperfumed hand dishwash formulation of Table 17.

The invention claimed is:

1. A compound of formula

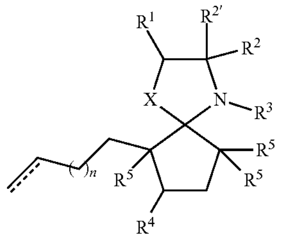

(I)

in the form of any one of its stereoisomers or a mixture thereof, and wherein n is 1, 2, 3 or 4;

the dotted line represents a single or a double bond,

X is an oxygen atom or a N—R group wherein R is a hydrogen atom, a $C_1$ to $C_4$ alkyl group, a phenyl group or a benzyl group, $R^1$ is a hydrogen atom or a $C_1$ to $C_{10}$ hydrocarbon group, optionally comprising from 1 to 5 oxygen atoms and/or one sulphur atom and/or one, two or three nitrogen atoms;

$R^2$ and $R^{2'}$ are, independently from each other, a hydrogen atom, a $C_1$ to $C_4$ alkyl group or a $CHR^1XH$ group, or $R^2$ and $R^{2'}$ when taken together form a carbonyl group;

$R^3$ is hydrogen atom, a methyl or an ethyl group;

$R^4$ is a hydrogen atom, a COOR' group or a $C_{1-3}$ alkyl group optionally substituted by a COOR' group wherein R' is a $C_{1-3}$ alkyl group;

$R^5$ are, independently from each other, a hydrogen atom or a methyl group; or

R and $R^1$, when taken together form a $C_{4-6}$ azocycloalkyl group; or $R^1$ and $R^2$; when taken together form a $C_{5-6}$ cycloalkyl group; or, $R^2$ and $R^3$, when taken together form a group of formula

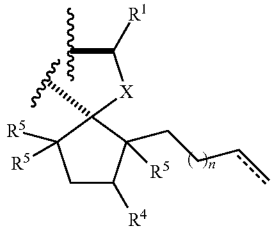

(II)

wherein the bold line is connected to the carbon atom of $R^2$ and the hatched line to the nitrogen atom of $R^3$.

2. The compound according to claim 1, wherein n is 2, 3 or 4 and wherein $R^4$ and $R^5$ are hydrogen atoms.

3. The compound according to claim 1, wherein X is a N—R group wherein R is a hydrogen atom, a methyl or an ethyl group, or R and $R^1$ are taken together to form a $C_{4-6}$ azocycloalkyl group.

4. The compound according to claim 1, wherein n is 3 and the dotted line is a double bond.

5. The compound according to claim 1, wherein $R^2$ is a methyl group or an ethyl group and $R^{2'}$ is a hydroxymethyl group, or $R^2$ and $R^{2'}$ are taken together and form a carbonyl group.

6. The compound according to claim 1, wherein $R^1$ is a hydrogen atom or a residue derived from an amino acid of formula $R^1CH(NH_2)COOH$.

7. The compound according to claim 1, wherein R and $R^1$ are taken together and form a $C_{4-5}$ azocycloalkyl group.

8. A method for providing a long-lasting odor imparted by perfumery ingredients derived from cyclopentanone to the environment, the method comprising adding a compound of formula (I) as defined in claim 1 as perfuming ingredient to the perfumery ingredients derived from cyclopentanone.

9. A method to confer, enhance, improve or modify the odor properties of a perfuming composition or of a perfumed article, which method comprises adding to said composition or article an effective amount of at least a compound of formula (I) as defined in claim 1.

10. A perfuming composition comprising:

i) as perfuming ingredient, at least one compound of formula (I) as defined in claim 1;

ii) at least one ingredient selected from the group consisting of a perfumery carrier and a perfumery base; and iii) optionally at least one perfumery adjuvant.

11. A perfumed consumer product comprising, as perfuming ingredient, at least one compound of formula (I), as defined in claim 1.

12. The perfumed consumer product according to claim 11, wherein the perfumery consumer product is a perfume, a fabric care product, a body-care product, an air care product or a home care product.

13. The perfumed consumer product according to claim 12, wherein the perfumery consumer product is a fine perfume, a liquid or solid detergent, a fabric softener, a fabric refresher, an ironing water, a shampoo, a coloring preparation, a hair spray, a deodorant or antiperspirant, a perfumed soap, shower or bath mousse, oil or gel, a hygiene product, an air freshener, a "ready to use" powdered air freshener or a hard-surface detergent.

14. A method of imparting a long-lasting or substantive odor imparted by perfumery ingredients derived from cyclopentanone to the environment or to surfaces; by adding at least one compound of formula (I) as defined in claim 1 to perfuming compositions or perfumed articles and applying them to the corresponding targeted environment or surface.

15. The compound according to claim 1, wherein $R^3$ is a hydrogen atom.

16. The compound according to claim 1, wherein:

X is a N—R group wherein R is a hydrogen atom, a methyl or an ethyl group;

$R^1$ is a hydrogen atom or a residue derived from an amino acid of formula $R^1CH(NH_2)COOH$;

or R and $R^1$ are taken together to form a C4-6 azocycloalkyl group;

$R^2$ is a methyl group or an ethyl group and $R^{2'}$ is a hydroxymethyl group, or $R^2$ and $R^{2'}$ are taken together and form a carbonyl group;

$R^3$ is a hydrogen atom, a methyl or an ethyl group; and n is 2, 3 or 4 and wherein $R^4$ and $R^5$ are hydrogen atoms.

17. A perfuming composition comprising:

i) as perfuming ingredient, at least one compound of formula (I) as defined in claim 16;

ii) at least one ingredient selected from the group consisting of a perfumery carrier and a perfumery base; and iii) optionally at least one perfumery adjuvant.

18. A perfumed consumer product comprising, as perfuming ingredient, at least one compound of formula (I) as defined in claim 16.

19. The perfumed consumer product according to claim 18, wherein the perfumery consumer product is a perfume, a fabric care product, a body-care product, an air care product or a home care product.

20. The compound according to claim 6, wherein $R^1$ is a residue derived from a natural α-amino acid selected from the group consisting of S-alanine, S-arginine, S-asparagine, R-cysteine, S-glutamine, glycine, S-histidine, S-isoleucine, S-leucine, S-lysine, S-methionine, S-phenylalanine, S-serine, S-threonine, S-tryptophane, S-tyrosine, S-valine, S-aspartic acid, and S-glutamic acid or from an artificial α-amino acid selected from the group consisting of norleucine, norvaline, 2-phenylglycine, ornithine, homoalanine, homocysteine, and homoserine.

* * * * *